(12) United States Patent
Erbeldinger et al.

(10) Patent No.: US 8,470,525 B2
(45) Date of Patent: Jun. 25, 2013

(54) METHOD FOR ANALYZING AIR

(75) Inventors: Markus Erbeldinger, Pittsburgh, PA (US); David B. Silcott, Reisterstown, MD (US); Jason Aaron Berberich, Pittsburgh, PA (US); Keith E. LeJeune, Export, PA (US)

(73) Assignee: Agentase, LLC, Pittsburgh, PA (US)

( * ) Notice: Subject to any disclaimer, the term of this patent is extended or adjusted under 35 U.S.C. 154(b) by 0 days.

(21) Appl. No.: 13/225,030

(22) Filed: Sep. 2, 2011

(65) Prior Publication Data

US 2013/0059319 A1  Mar. 7, 2013

(51) Int. Cl.
*C12Q 1/00* (2006.01)
(52) U.S. Cl.
USPC .................. 435/4; 435/20; 422/408
(58) Field of Classification Search
USPC ........................ 435/4, 20; 422/408
See application file for complete search history.

(56) References Cited

U.S. PATENT DOCUMENTS

| | | | | |
|---|---|---|---|---|
| 6,885,440 | B2 * | 4/2005 | Silcott et al. | 356/73 |
| 7,106,442 | B2 * | 9/2006 | Silcott et al. | 356/338 |
| 7,422,892 | B2 * | 9/2008 | LeJeune et al. | 435/288.7 |
| 2006/0238757 | A1 * | 10/2006 | Silcott | 356/338 |

* cited by examiner

*Primary Examiner* — Ralph Gitomer
(74) *Attorney, Agent, or Firm* — Buchanan Ingersoll & Rooney PC; Craig G. Cochenour

(57) ABSTRACT

A method and device are disclosed for continuously detecting, classifying and identifying toxic particles, aerosols and/or vapor in an air sample, in near real time by directing an air sample containing an optional target analyte, in the form of particles, aerosols and/or vapors, enzyme(s), and enzyme substrate(s), to a surface of a collection matrix for forming a biocatalytic reaction product of a plurality of freely mobile optical reporters, and by using a light source with optical reader to interpret the signal from the optical reporter, enabling the detection, classification and identification of toxic particles, aerosols and/or vapor in the air sample.

34 Claims, 12 Drawing Sheets

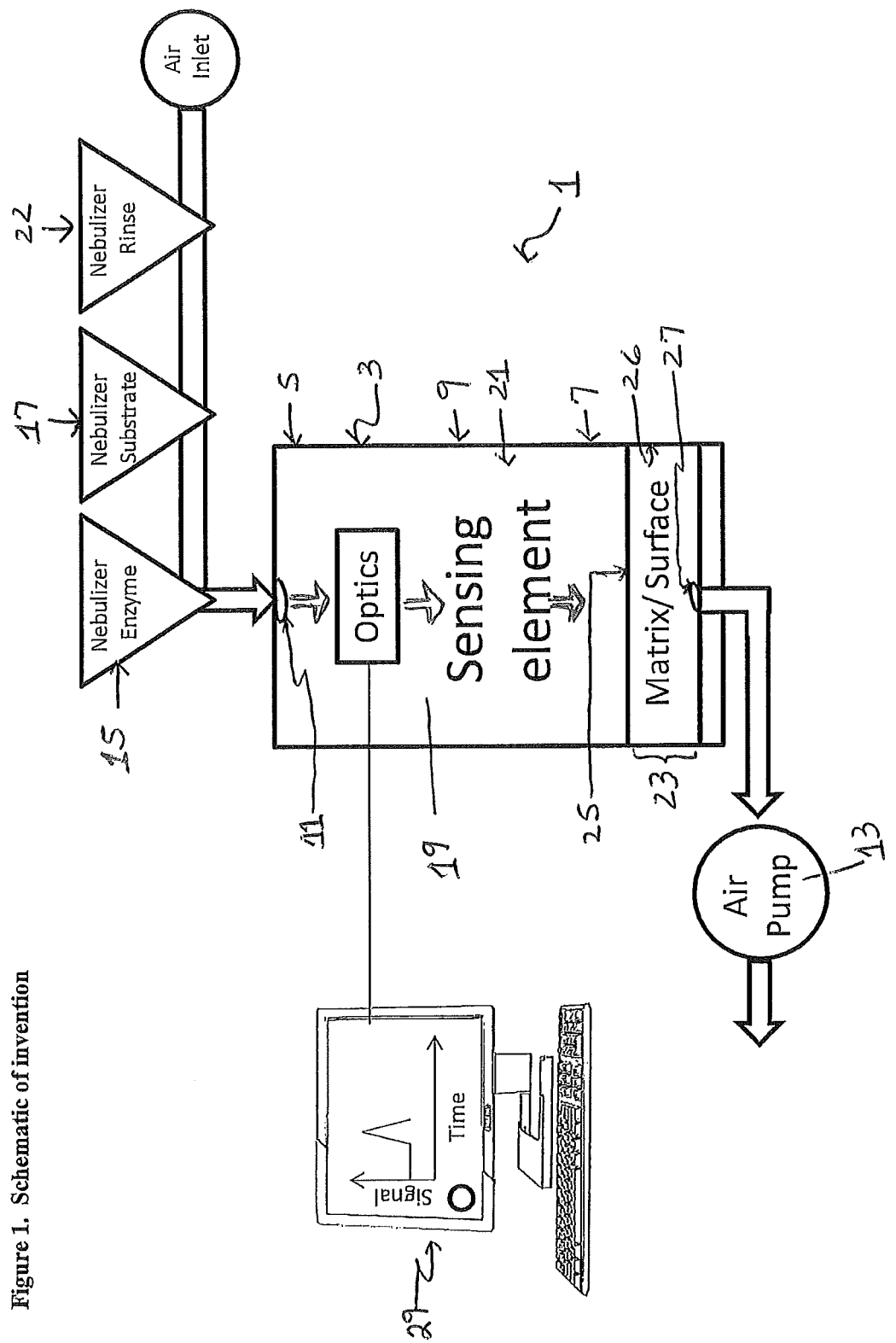
Figure 1. Schematic of invention

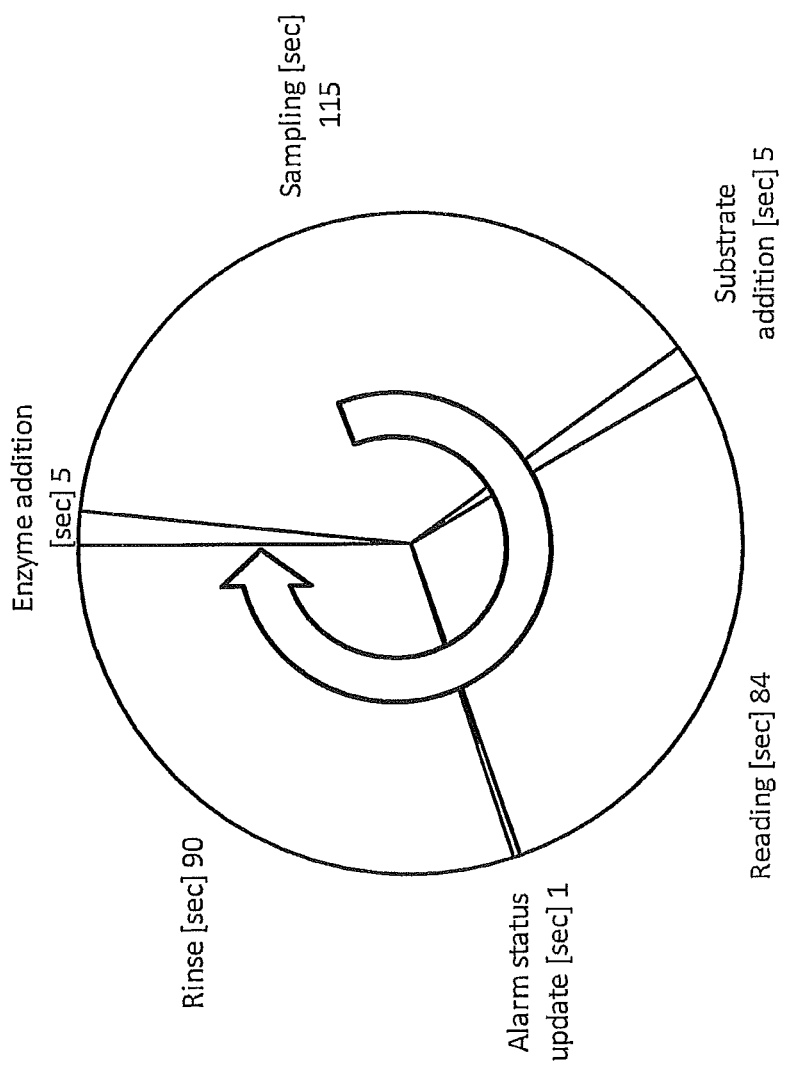
Figure 2. 300 second cycle

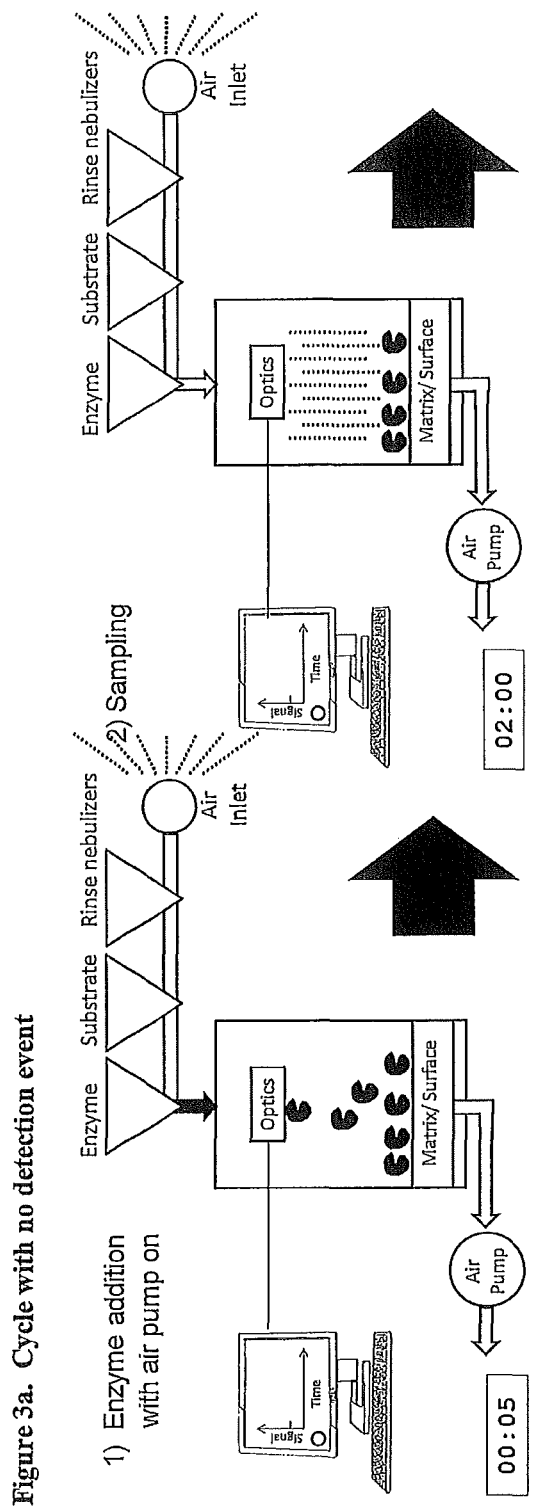

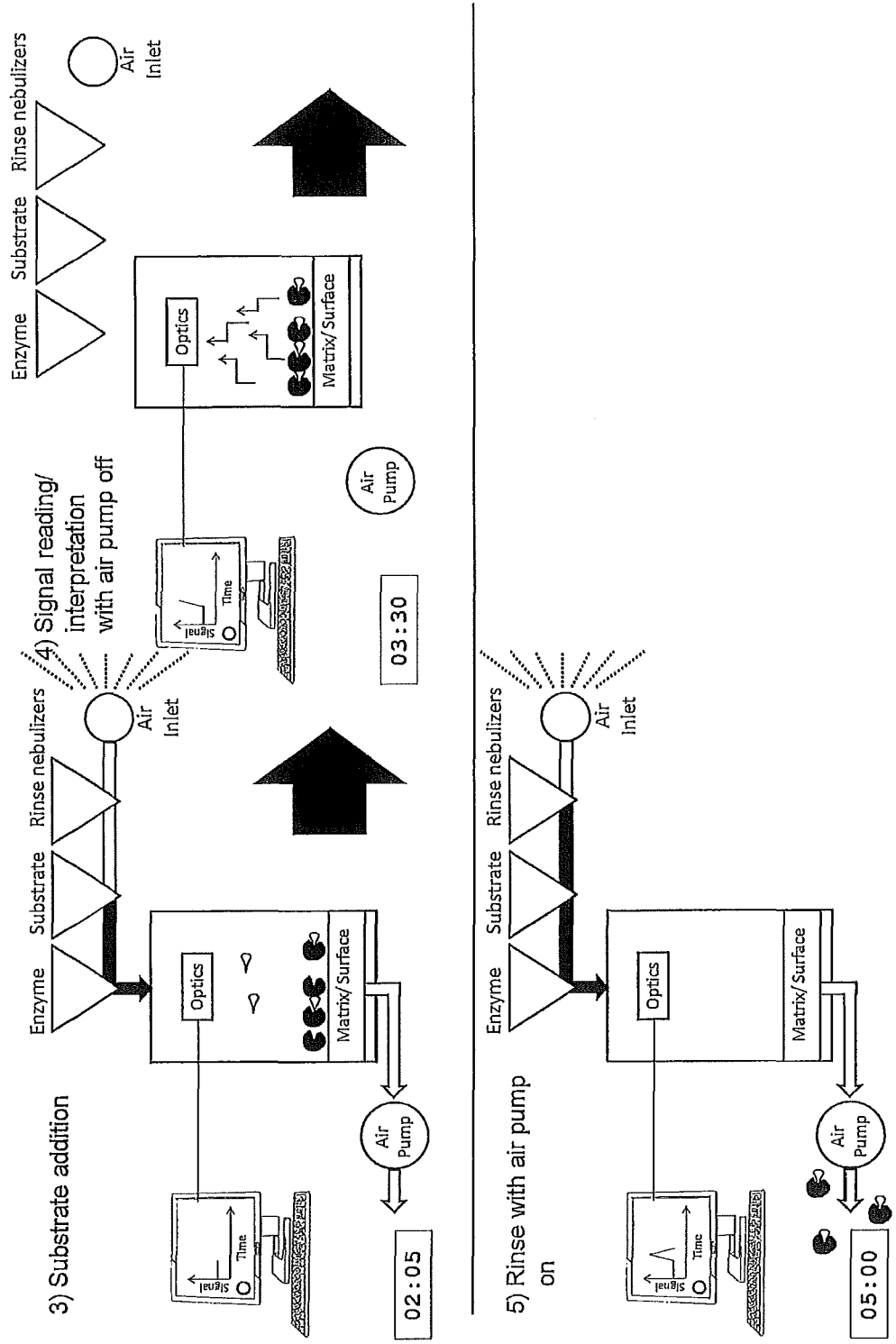

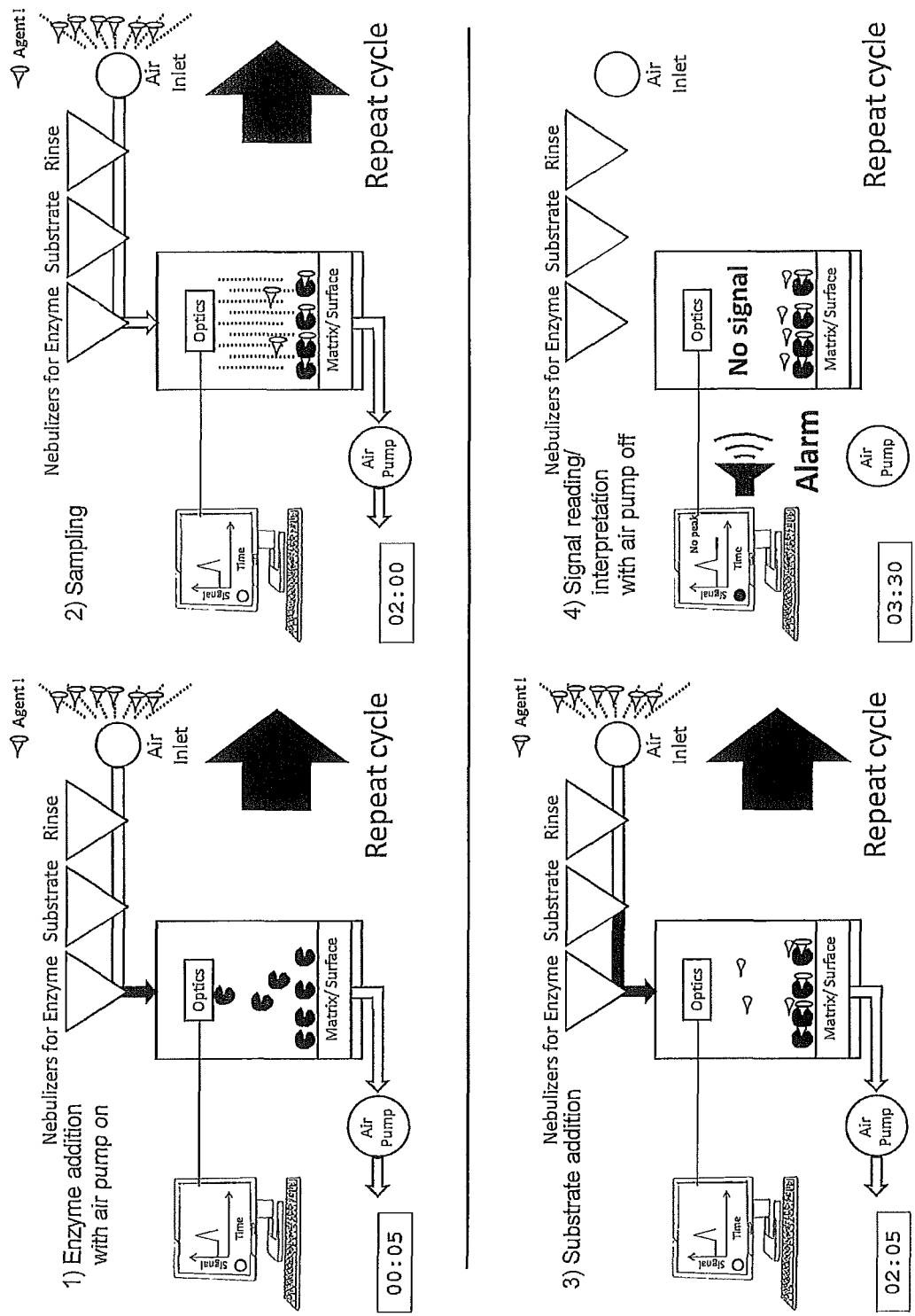
Figure 4. Cycle with detection event

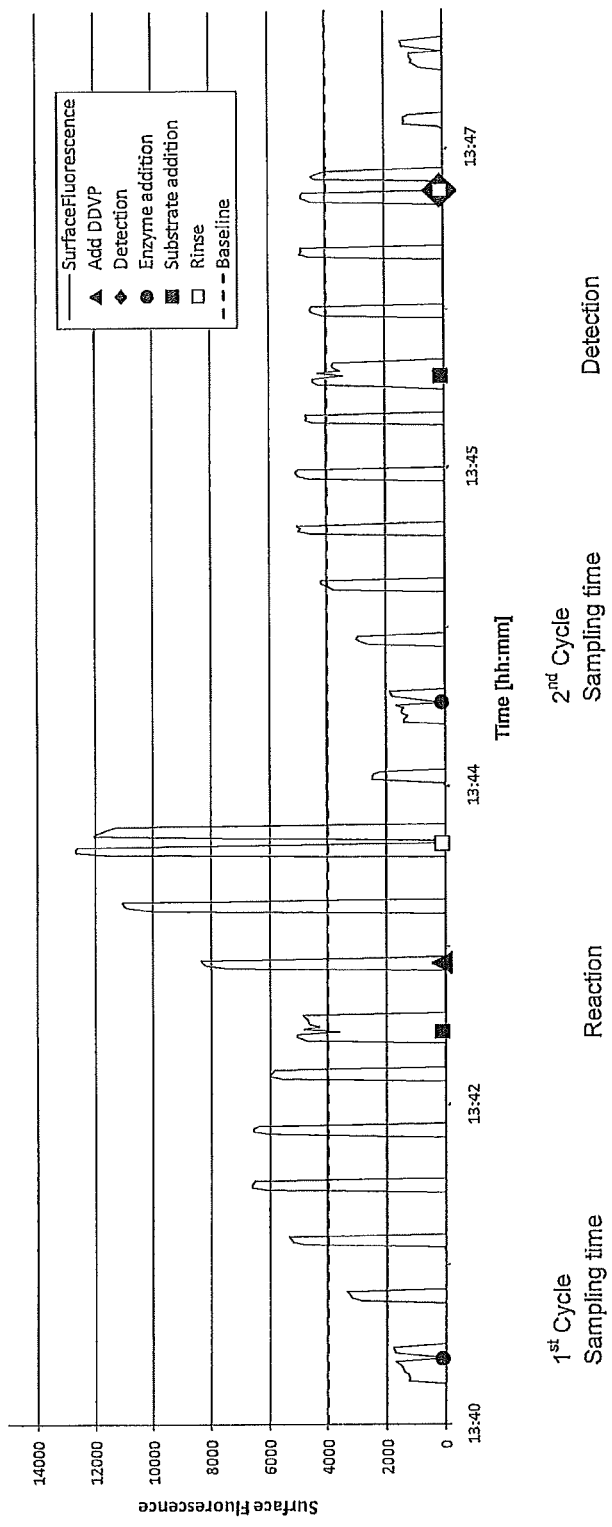
Figure 5. Data example 1- dichlorvos vapor detection

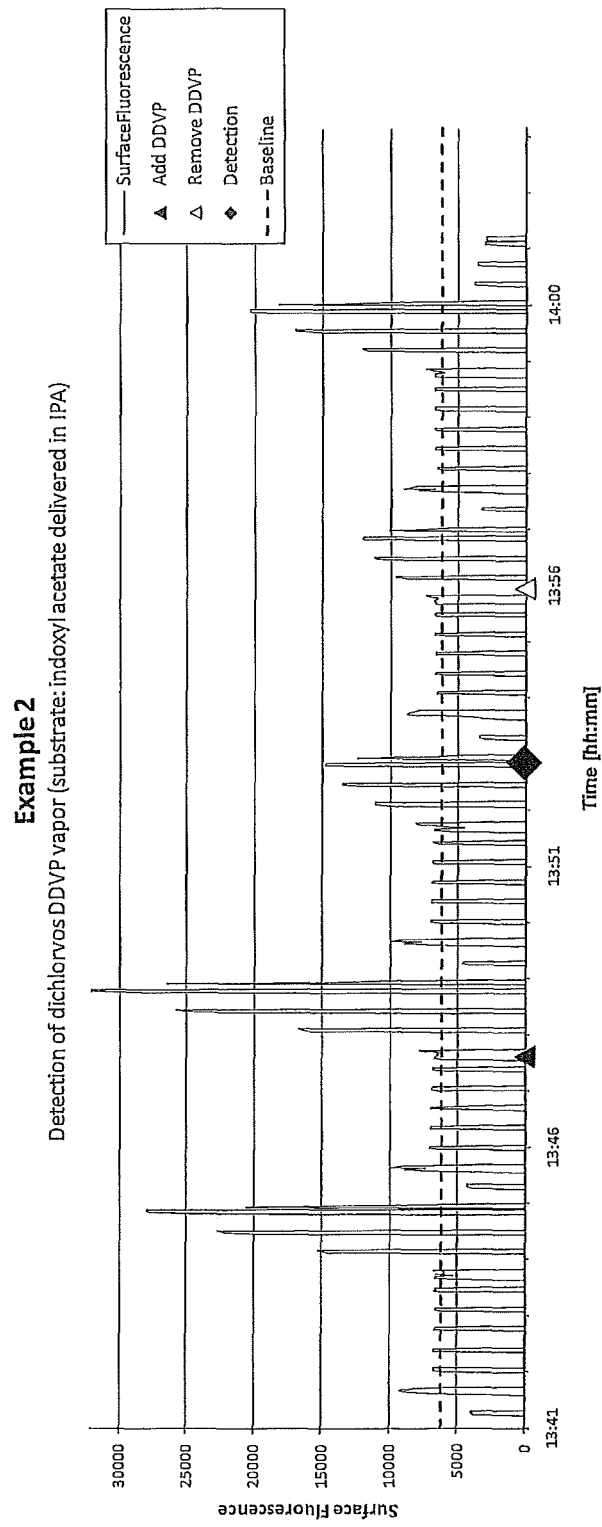
Figure 6. Data example 2 - dichlorvos vapor detection

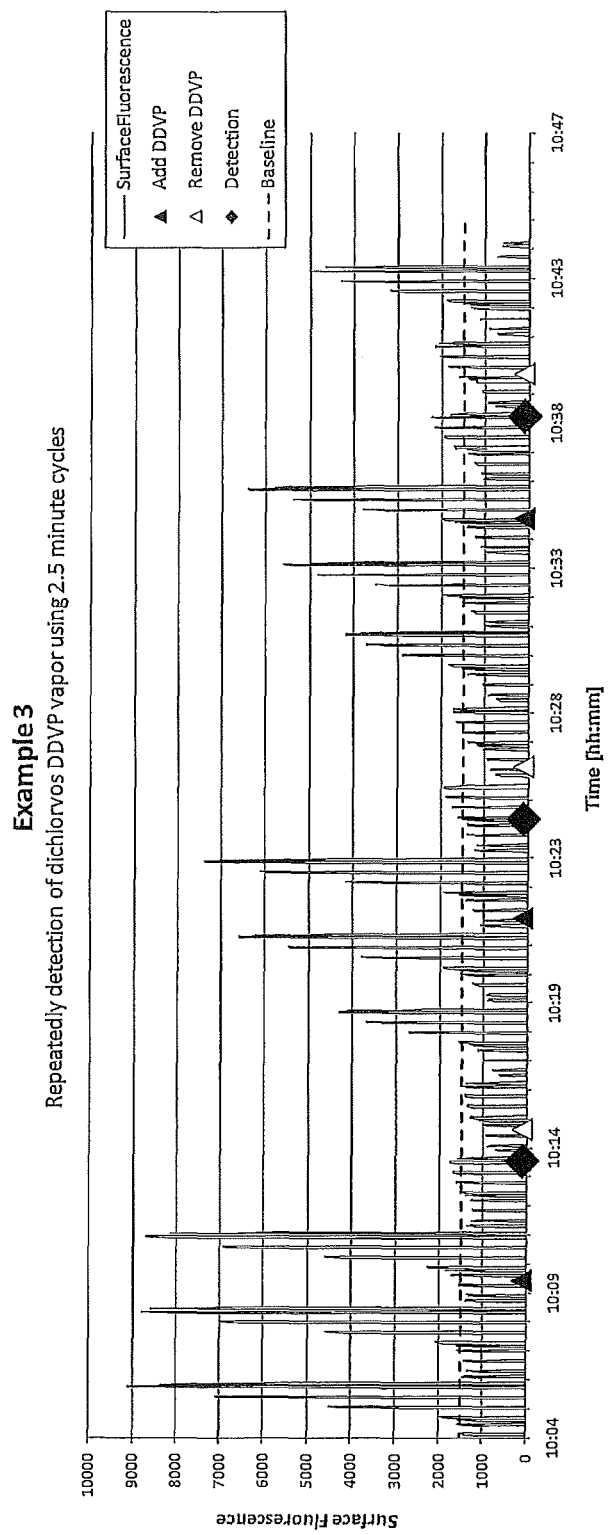
Figure 7. Data example 3 - dichlorvos vapor detection

Figure 8. Data example 4 – paraoxon aerosol detection

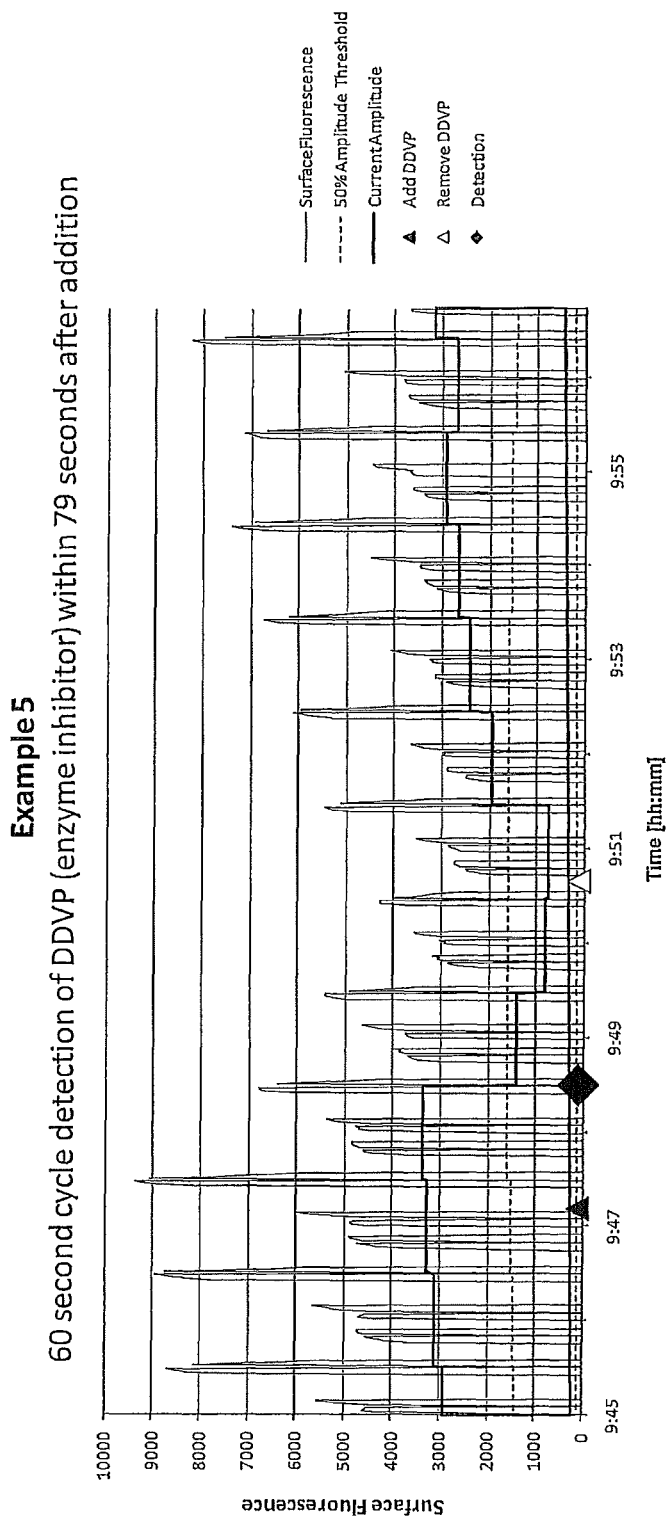
Figure 9. Data example 5 - dichlorvos vapor detection

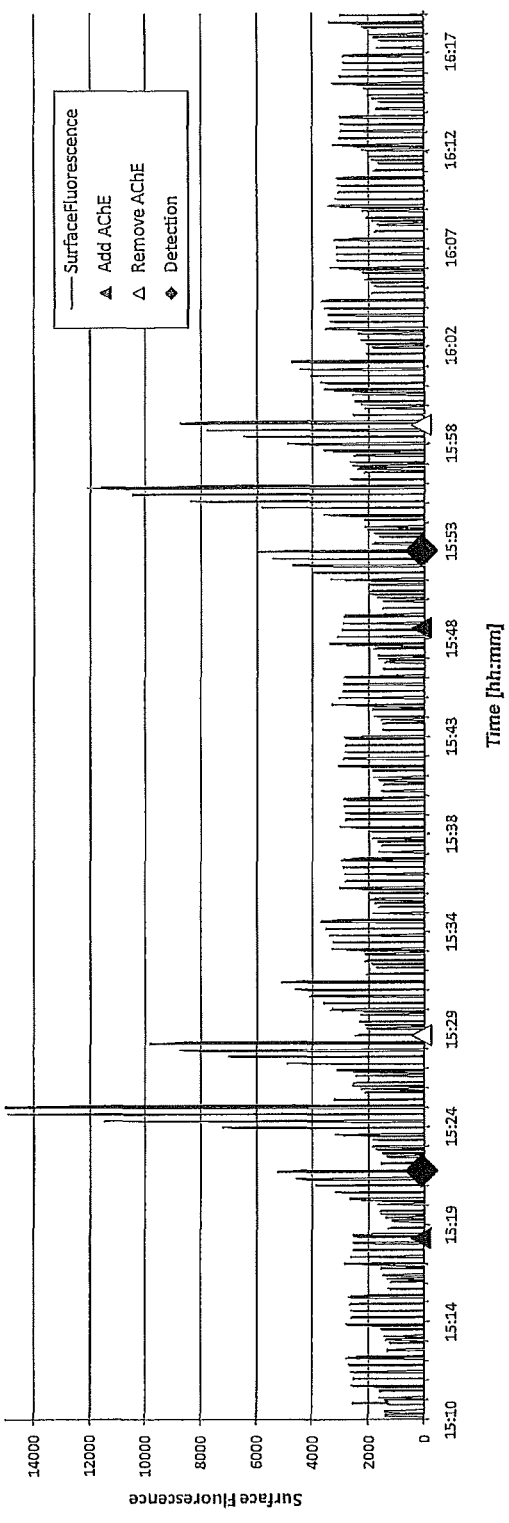
Figure 10. Data example 6 – AChE enzyme detection

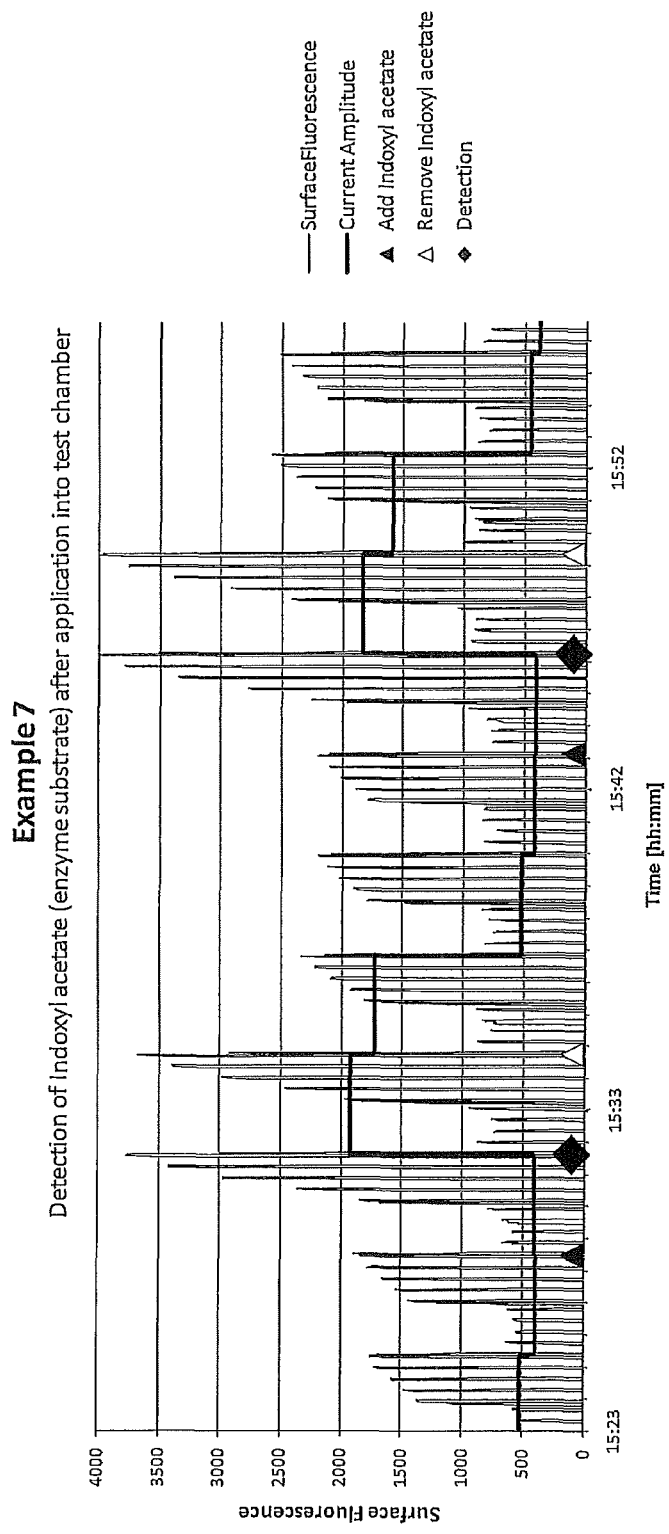
Figure 11. Data example 7 – indoxyl acetate detection

METHOD FOR ANALYZING AIR

GOVERNMENT INTEREST

Certain embodiments of this invention were made with Government support under Contract No. W911NF-08-D-0002 DO 0011 awarded by US Army RDECOM ACQ CTR and under Contract No. HSHQPA-05-9-0046 awarded by the Department of Homeland Security Science & Technology Directorate. The Government has certain rights in the invention.

FIELD OF THE INVENTION

The present invention relates to a device that is an air analyzer and a method that employs biocatalytic reactions to monitor air in near real time for the presence of particles, aerosols, and/or vapor, and especially to a method that employs an enzyme or enzymes to detect the presence of an enzyme inhibitor within the environment without the active involvement of the user.

BACKGROUND OF THE INVENTION

There is an urgent need for the early detection of a deliberate release of harmful, toxic materials in the air originating from acts of tenor, offensive military action or accidents. Those materials can be of chemical or biological nature. Those materials can be present in the form of aerosol, solid particles, and vapor, or a combination of aerosol, particles and vapor.

In order to minimize the harmful effects of those materials, an early, near real-time detection is essential at low concentrations allowing the early deployment of counter measures and evacuation prior to causing damage to humans or loss of human life. However, presently used technologies and devices have limitations in effectively achieving this early detection of such harmful chemicals or biological threats. Enzyme-based biosensors are most suitable for detection of toxins such as, for example, but not limited to, pesticides, acids, chemical warfare agents, and toxic industrial chemicals because enzymes can be selectively inhibited by a particular class of chemicals. Enzymes are highly specific biocatalysts which are typically not affected by other chemicals present and therefore provide a high resistance to interferences by other chemicals in the environment of question. Enzyme-based biosensors are also used in detecting target chemicals that act as substrates for enzymes. In most biosensors, the sensing enzymes are incorporated in devices such as electrodes, transducers, fiber optics, hydrogels, polymer sponges, or crystals, and the target chemical must be physically contacted with the device so as to enable its interaction with the sensing enzyme.

In general, six classes or types of enzymes (as classified by the type of reaction that is catalyzed) are recognized. Enzymes catalyzing reduction/oxidation or redox reactions are referred to generally as EC 1 (Enzyme Class 1) Oxidoreductases. Enzymes catalyzing the transfer of specific radicals or groups are referred to generally as EC 2 Transferases. Enzymes catalyzing hydrolysis are referred to generally as EC 3 hydrolases. Enzymes catalyzing removal from or addition to a substrate of specific chemical groups are referred to generally as EC 4 Lyases. Enzymes catalyzing isomeration are referred to generally as EC 5 Isomerases. Enzymes catalyzing combination or binding together of substrate units are referred to generally as EC 6 Ligases.

Enzymes have been known since the early 1960's to be useful tools for detecting the presence of chemical species. Rogers, K. R., *Biosensors Bioelectronics,* 10, 533 (1995). Generally all enzymatic biosensors function by one of two methods. The enzyme either converts an undetectable compound of interest into another or series of compounds which can be detected with a chemical-based sensor or the enzyme is inhibited by the presence of the compound of interest and the enzyme inhibition is linked to a measurable quantity.

As described above, many biosensors employ the principle of enzyme inhibition by certain class of chemicals. For example, organophosphates inhibit cholinesterases, cyanides inhibit peroxidases, and heavy metals inhibit ureases, and so on. These phenomena cause drastic changes in the chemical and/or physical state of the system and these changes are sensed by the read-out mechanism employed in various biosensors.

Similarly, many enzyme-based sensors detect the target analyte by utilizing the analyte itself as a substrate e.g. glucose, urea, creatinine etc. This phenomenon also causes physical/chemical changes in the sensory system of the biosensor used and enables detection of the target analyte. In the following paragraphs, we briefly review traditional known background enzyme based biosensors for a variety of target analytes, which are based either on enzyme inhibition or on enzyme catalysis.

Acetylcholinesterase Based Organophosphate Sensors:

Depending on the potency, phosphoesters of organic alcohols are used either as insecticides, pesticides or as nerve agents in chemical warfare. In both the applications, enzyme acetyl cholinesterase (AChE) in exposed organisms is irreversibly inhibited due to phosphorylation of serine hydroxyl group in the active site of the enzyme. Detection of trace amounts of organophosphates in agriculture and in civilian and military environment is an important area of research. Numerous amperometric and potentiometric sensors comprising AChE have been reported so far (N. Jaffrezic-Renault, Sensors 1, 60-74 (2001)). In these sensors AChE is immobilized on the surface of transducers through different techniques. In amperometric sensors the current generated by oxidation of thiocholine (which is generated by enzymatic hydrolysis of substrate butyrylthiocholine) is measured. Also, a bi-enzymatic system of AChE and choline oxidase has been used to detect organophosphates, wherein, hydrogen peroxide generated by oxidation of choline (which is generated by AChE catalyzed hydrolysis of acetylcholine) is detected. In case of potentiometric sensors such as ion selective electrodes (ISE) or ion sensitive field effect transistor (ISFET), organophosphates are detected by monitoring the change in the pH due to the acid generated from enzymatic hydrolysis of acetylcholine.

Recently, a photonic crystal-AChE based sensor for organophosphates has been reported. This sensor uses AChE immobilized in a polymerized crystalline colloidal array. When trace amounts of organophosphates inhibit AChE, the polymer swells and changes the lattice spacing in crystals causing red-shift in the wavelength of diffracted light (J. P. Walker, S. A. Asher, Anal. Chem. 77, 1596-1600 (2005)).

U.S. Pat. No. 7,008,524 describes the sensor and the method to detect chemical agents using metal interdigitized electrodes coated with polymer film containing AChE. When organophosphates react with AChE in the sensor, chemical and/or morphological changes occur in the polymer film and this modulates the electric current flowing through the electrode. U.S. Pat. No. 6,821,738 describes optical sensor based on reversible complex of AChE and porphyrins or phthalocyanines. When organophosphates react with AChE, they displace the fluorescent porphyrins from the active site of AChE. This causes changes in the absorption and/or fluorescence spectra of porphyrins that are detectable by spectrophotometers. U.S. Pat. No. 6,541,230 describes polyurethane sponges containing a covalently immobilized AChE, butyrylcholinesterase, organophosphorous hydrolase, and the indicator useful in "verified decontamination" of chemical warfare agents. U.S. Pat. No. 6,750,033 describes polyurethane polymer containing AChE (which is inhibited by organophosphates) and a second base-producing enzyme urease (which is not inhibited by organophosphates). In the absence of organophosphates, the polymer soaked in substrates solution has neutral pH as both the enzymes in the polymer are producing acid and base at controlled rates. When organophosphates are swiped onto the sensor, AChE in the polymer is inhibited and pH of the medium is increased. This is visualized by pH sensitive indicator dye incorporated in the polymer.

Organophosphorous Hydrolase Based Organophosphate Sensors:

Since AChE is irreversibly inhibited by organophosphates the sensors based on AChE are made for single use application. For reusable applications, researchers have developed sensors using organophosphorous hydrolases (OPH) which catalytically hydrolyze organophosphates as their substrates. Mulchandani et al have reviewed the present state of the art in OPH based biosensors which can be broadly categorized into potentiometric, optical and amperometric sensors (A. Mulchandani, W. Chen, P. Mulchandani, J. Wang, K. R. Rogers, Biosensors and Bioelectronics 16, 225-230 (2001)). Potentiometric sensor for organophosphates has been reported by immobilizing a layer of OPH crosslinked with bovine serum albumin and glutaraldehyde on to a pH electrode. The electrode measures change in the pH when it is in contact with the solution containing organophosphates (P. Mulchandani, A. Mulchandani, I. Kaneva, W. Chen, Biosensors and Bioelectronics 14, 77-85 (1999)).

Two different optical sensors containing OPH have been developed. In the first sensor, fluorescein isothiocyanate (FITC) labeled OPH was adsorbed on poly(methyl methacrylate) beads and the sensor beads were contacted with the analyte in a microbead fluorescence analyzer. The presence of organophosphates was detected by monitoring decrease in the fluorescence of FITC label on inhibited AChE. In the second optical sensor, a fiber optic set up was built with desired cut off wavelength of 348 or 400 nm to detect hydrolysis products of organophosphates such as coumaphos or p-nitrophenol, respectively. OPH was immobilized on a nylon membrane and attached to the optical fiber in the set up (A. Mulchandani, S. Pan, W. Chen, Biotechnol. Prog. 15, 130-134 (1999)).

OPH based amperometric sensor for organophosphates has been developed in the form of a screen-printed thick film carbon electrode. The electrode was coated with Nafion membrane containing OPH. p-nitrophenolate anion released by enzymatic hydrolysis of certain organophosphates was oxidized at the anode and the generated current was measured using a potentiostat (A. Mulchandani, P. Mulchandani, W. Chen, J. Wang, L. Chen, Anal. Chem. 71, 2246-2249 (1999)). In a modification of this technique, a remote OPH-based amperometric biosensor was also developed (J. Wang, L. Chen, A. Mulchandani, P. Mulchandani, W. Chen, Electroanalysis 11, 866-869 (1999)).

All these sensors have exhibited very low detection limits ranging between 0.5 to 50 µM concentrations of organophosphates. However, the operating mechanism of these sensors requires that each time the sample must be applied to the electrode or polymer in order to detect the presence of organophosphates. Thus, none of these background sensors are particularly conducive for fully automatic detection in the air. Biosensors comprising enzyme-electrodes and based on enzyme-inhibition have been also developed for drugs, cyanide, heavy metals, and chemicals.

Peroxidase Based Cyanide Sensors:

Horseradish peroxidase (HRP) is reversibly inhibited by cyanide ions. Therefore, HRP based biosensors have been constructed by many researchers to monitor the cyanide traces in water. For example, HRP immobilization on surface of ISFET has been reported (V. Volotovsky, N. Kim, Biosensors and Bioelectronics 13, 1029-1033 (1998)). The sensor was constructed by coating the electrode with HRP immobilized in poly(4-vinyl pyridine-co-styrene). The sensor was able to detect 0.6 µM potassium cyanide and was able to be reused after washing. Similarly, HRP based amperometric sensor has been reported by immobilizing the enzyme and an osmium redox polymer ([Os(bipyridyl)2(poly(vinyl pyridine)10Cl]Cl) on to an electrode. Upon addition of substrate hydrogen peroxide, a biocatalytic reduction generated the current. This current was inhibited by the analyte cyanide to cause change from 150 mV to 0 mV. Cyanide detection ranged between 4 µM to 40 µM (T-M. Park, E. I. Iwuoha, M. R. Smyth, Electroanalysis 9, 1120-1123 (1997)). A cyanide sensor electrode based on cytochrome oxidase has been also reported (A. Amine, M. Alafendy, J-M. Kauffmann, M. N. Pekli, Anal. Chem. 67, 2822-2827 (1995)). Here also, these sensors are limited to detect cyanide in aqueous samples and are not conducive to determine the presence of cyanide on surfaces.

Urease Based Heavy Metal Ion Sensors:

Urease is inhibited by toxic heavy metal ions such as mercury, lead, and cadmium. Thus, urease based sensors have been constructed to detect trace amounts of heavy metal ions in drinking water and industrial effluents. For example, a conductometric urease biosensor has been reported for detection of $Hg^{+2}$, $Cu^{+2}$, $Cd^{+2}$, and $Pb^{+2}$ ions (S-M. Lee, W-Y. Lee, Bull. Korean Chem. Soc. 23, 1169-1172 (2002)). The sensor was constructed by immobilizing the enzyme-silica sol-gel as a thick film on screen printed interdigitated array electrode. Inhibition of urease by heavy metal ions was measured from the difference in the admittance response for 1 mM urea before and after the interaction with metal ions. Also, urease based optical biosensor for heavy metals have been constructed by immobilizing the enzyme on aminopropyl glass. Heavy metals were detected by monitoring changes in pH resulting from urease catalyzed hydrolysis of urea before and after the incubation with metal ions (R. T. Andres, R. Narayanaswamy, The Analyst, 120, 1549-1554 (1995)).

Enzyme Based Toxic Chemical Sensors:

Amperometric sensors for detection of thiols, carbamates, thiourea, and benzoic acid have been reported by using tyrosinase and peroxidase electrodes (J. Wang, E. Dempsey, A. Eremenko, Anal. Chim. Acta 279, 203-208 (1993)). Aqueous solutions of enzyme and crosslinking polymer were applied to an electrode to form the enzyme-containing film layer around the electrode. Detection of chemicals was performed by measuring the current generated upon addition of 0.2 mM phenol before and after the incubation with the chemical.

Enzyme Based Sensors for Analytes Used as Substrates:

Urease catalytically hydrolyzes urea into ammonia, carbon dioxide and water. Urea can be present as adulterant in milk. Also, urea can be present in river water and in industrial effluents. Therefore, urease based biosensors have been developed to detect urea in various aqueous samples. For example, potentiometric urea sensor has been developed by coating the surface of a microelectrode with crosslinking mixture of urease, polyethyleneimine, and glutaraldehyde. The sensor exhibited short response time (15-30 seconds) and linear detection range of 1-100 mM urea (Lakard, B., Herlem, G., Lakard, S., Antoniou, A., Fahys, B., Biosensors and Bioelectronics 19, 1641-1647 (2004)).

Similarly, amperometric urea biosensor has been developed by immobilizing urease-containing conducting polymer film of poly((N-3-aminopropyl pyrrole-co-pyrrole) onto an electrode (Bisht, R. V., Takashima, W., Kaneto, K., Biomaterials 26, 3683-3690 (2005)). The electrode measured the redox current generated by pH sensitive redox compound hematein. The electrode gave linear response in the range of 0.16-5.0 mM urea in aqueous medium.

For diabetic patient populations, glucose is an important analyte detected by glucose oxidase based biosensors that oxidize the substrate glucose into gluconic acid. A variety of blood glucose sensors are available in the market that are based on glucose oxidase. Apart from this, there is continuously ongoing research in the field of glucose sensors to improve sensor operations and patient comfort levels. For example, glucose sensing contact lens has been reported to monitor glucose levels in tears (Badugu, R., Lakowicz, J. R., Geddes, C. D. Journal of Fluorescence 13, 371-373 (2003)). The contact lens uses boronic acid containing flourophore which reacts with vicinal diols in glucose and changes its fluorescence to detect 0.05-1.0 mM glucose in tears, which can be tracked to 5-10 fold higher glucose level in the blood.

Creatinine is yet another important health-biomarker which can be detected using enzyme based sensors. For example, potentiometric biosensor for creatinine has been reported by using electrode modified with creatinine deiminase, the enzyme that degrades creatinine to produce ammonia (Shih, Y., Huang, H., Anal. Chim. Acta 292, 143-150 (1999)). Interestingly, creatinine amidohydrolase, the enzyme that converts creatinine into creatine has been also used to develop an amperometric biosensor (Berberich, J. A., Chan, A., Boden, M., Russell, A. J., Acta Biomaterialia 1, 193-199 (2005).

The development of monitoring devices for sampling and for chemical identification and detection has also been previously put to practice. Much of the art related to device development focuses on equipment for use in laboratories as automated samplers or fluid handling equipment. U.S. Pat. Nos. 4,224,033 and 4,338,280 each describe fluid handling devices that facilitate hands-free processing of individual samples in a preparatory fashion for later analysis and evaluation. Similarly, U.S. Pat. No. 4,066,412 discloses a device that can carry disposable reagents to aid in monitoring the physical properties of a reaction mixture by passing through a fixed path length.

Other background art describes devices that employ specialized components to facilitate the use of particular sensing chemistries and protocols for fluid analysis. U.S. Pat. No. 4,826,759 describes a fluid sampling device that carries two absorbent layers that are used to bring fluid components into the device and transfer such elements to a second layer for chemical analysis. U.S. Pat. Nos. 4,726,929 and 4,958,295, describe modular devices that handle and analyze fluids in unique ways including disposable collection modules and internal vacuum drives, respectively.

U.S. Pat. No. 4,525,704 describes the use of cholinesterase and electrical currents in detecting toxic gases. Other patents describe devices that can be used to detect the presence of enzyme substrates within a specified sample. U.S. Pat. No. 5,223,224 describes an arrangement for flow injection analysis which sample gases are kept isolated from the environment within the device. U.S. Pat. Nos. 5,504,006 and 5,994, 091 both describe sensor devices to sample gas and liquid streams, respectively, for enzyme substrates by linking enzyme activity brought on by the presence of substrate to a colorimetric signal. U.S. Pat. No. 7,422,892 B2 describes another device that employs an enzyme and substrate pair to continuously monitor an incoming sample for the presence of an enzyme inhibitor. This sensor includes an immobilized enzyme that is selected to be inhibited by the analyte. This device also includes a mechanism to continuously or semi-continuously deliver a substrate compound to the immobilized enzyme.

All of the background art mentioned above for enzyme based sensors can detect the analyte of interest when it is present in the sample solution applied to the sensor. But none of these background art sensors have the ability to detect the analyte present in the air at near real-time and at very low concentrations, or to detect analyte present in the form of vapor, aerosol and solid particles. Therefore there is a great need in the commercial marketplace to provide a device and a method to monitor air in near real time for the presence of particles, aerosols and/or vapor, and especially for a device that employs an enzyme or enzymes to detect the presence of an enzyme inhibitor within the environment without the active involvement of the user.

U.S. Patent Publication. No 2006/0238757 A1 ("Silcott US Pub. '757) describes a device for detecting, classifying and identifying airborne biological and non-biological particles on an individual basis in near real-time, based on a single particle's intrinsic optical properties. However, this device has several shortcomings. Silcott US Pub. '757 describes a method requiring a reaction environment between the sampled airborne particles and optical reporters pre-reacted with selected markers wherein the reacted optical reporters are adsorbed onto the surface of an aerosol particle. Further, the method disclosed in Silcott US Pub. '757 does not concern itself with providing a cyclic process of continued detection. Silcott US Pub. '757 teaches at great lengths processes for establishing attachment via adsorption of the pre-reacted optical reporter to the surface of the sampled airborne particles. Specifically, Silcott US Pub. '757 teaches a reaction environment between the sampled airborne particles and the pre-reacted optical reporters that is created by either growing a liquid layer onto the airborne sample's particle's surface using evaporation/condensation, molecular sublimation or aerosol coagulation techniques, or by collecting airborne particles and introducing the collected particles to a liquid thin-film. Silcott US Pub. '757 teaches techniques for controlling the thickness and chemical composition of the liquid layer so that the optical reporter, solvent, and other required reagents are successfully adsorbed onto the surface of the aerosol airborne particle. Reacted and non-reacted airborne particles are introduced one at a time in the optical sensor of Silcott US Pub '757 for detection.

Therefore, a need exists for improved methods and devices for detecting, classifying, and identifying airborne biological and non-biological particulates, and discriminating specific biological and non-biological particulates from commonly encountered background particulates.

SUMMARY OF THE INVENTION

The present invention provides a device (sensor) and a method for detecting, classifying, and identifying a target analyte in air.

In one embodiment of this invention, a method for detecting, classifying, and identifying a target analyte is provided comprising the steps of providing an air flow mechanism for continuously or intermittently delivering an air sample optionally containing a target analyte to a reaction zone wherein the reaction zone has a first end and a second end and a middle section disposed between the first end and the second end, wherein the reaction zone has at least one opening for receiving the air sample; providing a collection matrix having a surface within or in juxtaposition to the reaction zone; establishing a direction of air flow of the air sample from the opening of the reaction zone towards the surface of the collection matrix; introducing through the opening of the reaction zone either continuously or intermittently at least one freely mobile enzyme, and at least one freely mobile substrate to the air sample, wherein the freely mobile enzyme, and the freely mobile substrate are in a nebulized, aerosolized, gaseous, or aqueous form; and providing for the entrainment of the freely mobile enzyme, and the freely mobile substrate with the air sample in the reaction zone for producing a biocatalytic chemical reaction of the air sample, the enzyme, the substrate, and optionally the target analyte, for forming a biocatalytic reaction product of a plurality of biocatalytic optical reporters without effecting adsorption of the optical reporter onto a surface of the air sample and optional target analyte. The method further comprises directing the air flow within the reaction zone with the plurality of the biocatalytic optical reporters in the direction of the surface of the collection matrix for contacting the surface of the collection matrix with at least one of the plurality of the biocatalytic optical reporters; providing at least one wave excitation source to generate and emit at least one discrete wavelength of light; directing at least one of the discrete wavelengths of light to the surface of the collection matrix having at least one of the plurality of the biocatalytic optical reporters; providing one or more detectors for reading (i) a signal of reflected, absorbed light or a light response from said one or more optical reporters located on the surface of the collection matrix, or (ii) an absence or suppression of a signal of reflected, absorbed light or absence or suppression of a light response from the one or more optical reporters located on the surface of the collection matrix; detecting (i) an increase or a decrease of the presence of the signal, or (ii) an absence of the signal; and providing at least one of a product rinse in an aerosol, nebulized or gaseous form to the surface of the collection matrix for removing the air sample, the enzyme, the substrate, the optional target analyte if any, and the biocatalytic optical reporters from the reaction zone and the collection matrix, and forming a spent product rinse comprising the air sample, the enzyme, the substrate, the optional target analyte if any, and the biocatalytic optical reporters for effecting regeneration of the collection matrix for reuse; and evacuating the spent product rinse from the reaction zone and the collection matrix via at least one of the openings in the reaction zone for completing one cycle of detection; and optionally repeating one or more cycles of the above steps.

In a preferred embodiment of this invention, the method includes wherein the surface of the collection matrix is a porous material. The porous material is elected from the group consisting of a polymer, vegetable fibers (paper), lignin, and cellulose, and combinations thereof. More preferably, the method provides wherein the porous material is a polymer that is selected from the group consisting of a polypropylene and a polyethylene, and combinations thereof.

Another embodiment of the method comprises providing wherein said one or more openings of the reaction zone are resealable openings for effecting a sealed engagement with the reaction zone and, alternatively, an unsealed relationship with the reaction zone, such that the opening of the reaction zone may be (i) opened when delivery of each of said air sample and the optional target analyte, the freely mobile enzyme, and the freely mobile substrate is desired to the reaction zone, and wherein the opening of the reaction zone may be subsequently (ii) closed when desired for example when the entrainment of the air sample and target analyte, the freely mobile enzyme, and the freely mobile substrate occurs in the reaction zone for producing the biocatalytic chemical reaction for forming the biocatalytic reaction product of a plurality of optical reporters.

Preferably, the method of the present invention as described herein, includes providing the direction of air flow within the reaction zone at a ninety degree angle from the first end of the reaction zone towards the surface of the collection matrix.

The method includes providing a freely mobile enzyme that is selected from the group of an oxidoreductase, a transferase, a hydrolase, a lyase, and an isomerase. Preferably, the freely mobile enzyme is an acetylcholinesterase or a butyrylcholinesterase and the target analyte is a cholinesterase inhibitor. Preferably the freely mobile substrate is selected from the group consisting of an acetylcholine, a butyrylcholine, an indoxylactetate, and a resofurin, and wherein the freely mobile enzyme is selected from the group of an acetylcholinesterase and a butyrylcholinesterase. Another embodiment of the present method includes providing a freely mobile substrate that is a benzoyl-arginine-ethyl-ester and a freely mobile enzyme that is a papain. A further embodiment of the present method includes providing a freely mobile substrate that is an urea and a freely mobile enzyme that is an urea aminohydrolase.

In a more preferred embodiment of this invention, the method includes alternating the flow of intermittent delivery of the air sample, the freely mobile enzyme, and the freely mobile substrate, respectively, in any order of addition, to the reaction zone to form a cycle of entrainment of the freely mobile enzyme and freely mobile substrate, with the air sample and optionally the target analyte, in the reaction zone to produce a plurality of the optical reporters. More preferably, the method includes providing the intermittent addition of the freely mobile enzyme initially to the reaction zone, followed by the intermittent addition of the freely mobile enzyme substrate to the reaction zone to form a cycle of entrainment of the freely mobile enzyme and freely mobile substrate, with the air sample and optionally the target analyte, in the reaction zone to produce a plurality of the optical reporters.

In another embodiment of this invention, the method includes providing a computer for recording and storing data that is read from the detector. The method includes analyzing the data stored on the computer. In a preferred embodiment, the method includes wherein the data is directly output from the detector. In a more preferred embodiment, the method includes wherein the data is wirelessly transmitted by the detector.

Another embodiment of this invention includes delivering the freely mobile enzyme, the freely mobile substrate, and the air sample and the optional analyte in any order of addition, or simultaneously, to the reaction zone.

In another embodiment of this invention, an enzyme-based air monitoring device (sensor) is provided for detecting a target analyte in air comprising at least one chamber having a first end and a second end and a middle section disposed between the first end and the second end, wherein the chamber has at least one opening located at the first end of the chamber; a mechanism for providing an air flow within the chamber for continuously or intermittently delivering an air sample optionally containing a target analyte to the first end of the chamber through the opening in the chamber; a mechanism for delivering a freely mobile enzyme to the air flow within the chamber containing the air sample and the optional target analyte, wherein the freely mobile enzyme is in a nebulized, aerosolized, or gaseous form; a mechanism for delivering a freely mobile substrate to the air flow within the chamber containing the air sample and the optional target analyte, wherein the freely mobile substrate is in a nebulized, aerosolized, gaseous, or aqueous form; a chemical reaction zone located within an interior of the chamber for the entrainment of the freely mobile enzyme, and the freely mobile substrate, within the air sample containing an optional target analyte for producing a biocatalytic reaction product of a plurality of biocatalytic optical reporters, without adsorption of the enzyme onto a surface of the air sample and/or the optional target analyte; a collection matrix located within the chamber and positioned below the chemical reaction zone, the collection matrix having a surface located within the interior of the chamber or in juxtaposition to the interior wall of the chamber; a mechanism for directing the air flow containing at least one of the biocatalytic optical reporters to the surface of the collection matrix; at least one wave excitation source for generating and emitting at least one discrete wavelength of light; a mechanism for directing at least one discrete wavelength of light to the surface of the collection matrix having at least one of the biocatalytic optical reporters; at least one detector for (a) reading (i) a signal of reflected, absorbed light or a light response from at least one of the plurality of the optical reporters located on the surface of the collection matrix, or (ii) an absence or suppression of a signal of reflected, absorbed light or absence or suppression of a light response from at least one of the plurality of the optical reporters located on the surface of the collection matrix, and (b) detecting (i) an increase or a decrease of the presence of the signal, or (ii) an absence of the signal; and a mechanism for evacuating the air sample, the optional target analyte, the freely mobile enzyme, the freely mobile substrate, and the biocatalytic optical reporters from the chamber and the collection matrix through the opening. Preferably, the device further includes a computer for reading and storing the data output from the detector and for analyzing the data to determine if the air sample is contaminated with the target analyte.

A preferred embodiment of the device of the present invention includes wherein the mechanism for providing the air flow within the chamber, the mechanism for delivering the freely mobile enzyme to the air sample, the mechanism for delivering the freely mobile substrate, and the mechanism for directing the air flow to the surface of the collection matrix is selected from the group of a fan, an air pump, a vacuum, and combinations thereof.

There are a number of specific operational and hardware requirements for a viable monitoring device. Enzyme activity and substrate activity must be maintained during operation. The enzyme must have sufficient thermal stability to maintain high levels of catalytic activity under normal operating conditions and temperatures. The enzyme substrates that are to be delivered to the reaction zone must be capable of being packaged in a manner that they are stable for extended periods of time without special storage conditions in order for the operation of the enzyme-based continuous air monitoring device to be practicable. Enzyme substrates must also be stable within the device for extended periods of time (such as for example, from a month to a year of time) under operational conditions.

BRIEF DESCRIPTION OF THE DRAWINGS

FIG. 1 is a schematic of a preferred embodiment of the device of the present invention.

FIG. 2 is a schematic of a 300 seconds cycle illustrating the different phases of operation of a preferred embodiment of the method of this invention.

FIGS. 3a and 3b illustrates the various steps of a preferred embodiment of the method of this invention comprising the cyclic operation with no detection event.

FIG. 4 illustrates the cycle shown in FIG. 2 with a detection event in a preferred embodiment of the method of this invention.

FIG. 5 illustrates the data output of Example 1 and shows the detection of dichlorvos DDVP vapor.

FIG. 6 illustrates the data output of Example 2 showing the detection of dichlorvos DDVP vapor in a different embodiment of the method of this invention using the substrate indoxyl acetate.

FIG. 7 illustrates the data output of Example 3 showing the detection of dichlorvos DDVP vapor in another embodiment of the method of this invention using a 2.5 minute cycle with multiple consecutive detection events and an aqueous based substrate.

FIG. 8 illustrates the data output of Example 4 showing the detection of paraoxon aerosol.

FIG. 9 illustrates the data output of Example 5 showing the detection of dichlorvos DDVP vapor in another embodiment of the method of this invention demonstrating the operation in 60 seconds cycles.

FIG. 10 illustrates the data output of Example 6 showing the detection of an enzyme protein specifically acetylcholinesterase (AChE) enzyme.

FIG. 11 illustrates the data output of Example 7 showing the detection of an enzymatic substrate specifically indoxyl acetate.

DETAILED DESCRIPTION OF THE INVENTION

A method for detecting, classifying, and identifying a target analyte in air is provided comprising the steps of providing an air flow mechanism for continuously or intermittently delivering an air sample optionally containing a target analyte to a reaction zone wherein the reaction zone has a first end and a second end and a middle section disposed between the first end and the second end, wherein the reaction zone has at least one opening for receiving the air sample; providing a collection matrix having a surface within or in juxtaposition to the reaction zone; establishing a direction of air flow of the air sample from the opening of the reaction zone towards the surface of the collection matrix; introducing through the opening of the reaction zone either continuously or intermittently at least one freely mobile enzyme, and at least one freely mobile substrate to the air sample, wherein the freely mobile enzyme, and the freely mobile substrate are in a nebulized, aerosolized, gaseous, or aqueous form; providing for the entrainment of the freely mobile enzyme, and the freely mobile substrate with the air sample in the reaction zone for producing a biocatalytic chemical reaction of the air sample, the enzyme, the substrate, and the optional target analyte if any, for forming a biocatalytic reaction product of a plurality of freely mobile biocatalytic optical reporters, without adsorption of the enzyme onto a surface of the air sample and the optional target analyte; directing the air flow within the reaction zone with the plurality of the biocatalytic optical reporters in the direction of the surface of the collection matrix for contacting the surface of the collection matrix with at least one of the plurality of the biocatalytic optical reporters; providing at least one wave excitation source to generate and emit at least one discrete wavelength of light; directing at least one of the discrete wavelengths of light to the surface of the collection matrix having at least one of the plurality of the biocatalytic optical reporters; providing one or more detectors for reading (i) a signal of reflected, absorbed light or a light response from the one or more optical reporters located on the surface of the collection matrix, or (ii) an absence or suppression of a signal of reflected, absorbed light or absence or suppression of a light response from the one or more optical reporters located on the surface of the collection matrix; detecting (i) an increase or a decrease of the presence of the signal, or (ii) an absence of the signal; and providing at least one of a product rinse in an aerosol, nebulized or gaseous form to the surface of the collection matrix for removing the air sample, the enzyme, the substrate, the optional target analyte if any, and the biocatalytic optical reporters from the reaction zone and the collection matrix, and forming a spent product rinse comprising the air sample, the enzyme, the substrate, the optional target analyte if any, and the biocatalytic optical reporters for effecting regeneration of the collection matrix for reuse; evacuating the spent product rinse from the reaction zone and the collection matrix via at least one of the openings in the reaction zone for completing one cycle of detection; and optionally repeating one or more cycles of the above steps.

The method further includes delivering the air sample to the reaction zone either passively or actively. In another embodiment, the method includes delivering the air sample to the reaction zone wherein the air sample is a collected air sample.

It will be appreciated by those persons skilled in the art that numerous methods exist in the background art for generating nebulized and aerosilized chemicals. Such methods include nanometer to micron size aerosols including electrospray and air atomization. With electrospray atomization, a nanometer to micron size diameter aerosol can be generated by operating an electrospray system in the cone-jet mode, as known by those persons skilled in the art. This is achieved when a liquid meniscus supported at the tip of a capillary tube is charged to a high electrical potential. Under the appropriate conditions the liquid turns to a cone whose apex emits a microscopic liquid filament that carries a certain current and flow rate. The cone-jet then breaks up into an electrospray of droplets, often in a monodisperse form, with diameters of the droplets being controlled with a diameter of a few nanometers to hundreds of microns. The size of the droplets is primarily controlled through the electrical conductivity of the liquid and the flow rate. See Rossell-Lompart and Fernandez De La Mora (1994), Kaufmann et al (1995), Fernandez De La Mora (1992), and Fernandez De La Mora and Loscertales (1994) for more detail on the process of Taylor cone generation. U.S. Pat. No. 6,802,456 also provides a tutorial on electrospray techniques. Air atomization, as known by those skilled in the art, involves the introduction of a liquid either by aspiration gravity or pressure fed to a high velocity air stream. under these conditions, the liquid is broken up into a polydisperse distribution of droplets with diameters spanning from tens of nanometers to hundreds of microns depending on the conditions. Other aerosol generation techniques including droplet formation via the oscillation of a metal disc containing microscopic holes via the use of small micron sized diameter tubes with liquid fed through at high velocities and via heated capillary tubes are known by those persons skilled in the art. U.S. Pat. Nos. 6,814,071; 6,782,886; 6,701,921; 6,586,390; 6,234,167; 5,743,251; and 5,586,550, to name a few, provide tutorials on aerosol generation.

Another embodiment of the present invention provides a method including a temperature controlled reaction zone having a temperature ranging from zero degrees Centigrade to ninety five degrees Centigrade. A further embodiment of this invention, as described herein, includes providing a separate storage zone for housing the freely mobile enzyme and a separate storage zone for housing the freely mobile substrate. Each storage zone is operatively connected to an air sample flow conduit. One end of the air sample flow conduit is operatively connected to the exterior wall of the chamber at the location of the opening. When the opening of the chamber (i.e. the opening leading to the reaction zone of the chamber) is in the unsealed state, the air flow proceeding through the air sample flow conduit in the direction of the opening of the reaction zone enters the opening and flows into the reaction zone of the chamber. In a preferred embodiment of this invention, each separate storage zone is temperature controlled such that the storage zone for each of the enzyme and each of the enzyme substrate each have a temperature ranging from zero degrees Centigrade to ninety five degrees Centigrade.

In a preferred embodiment of this invention, the method includes wherein the surface of the collection matrix is a porous material. The porous material is, for example, but not limited to, any material that has pores or vessels and that is capable of being penetrated. More preferably, the porous materials of this invention is a material selected from the group consisting of a synthetic or a natural occurring polymer, a vegetable fiber, a paper, a lignin, and a cellulose, and combinations thereof. Most preferably, the porous material is a polymer that is selected from the group consisting of a polypropylene and a polyethylene, and combinations thereof.

In another embodiment of this invention, the method, as described herein, includes providing wherein one or more openings of the reaction zone are resealable openings for effecting a sealed engagement with the reaction zone and an unsealed relationship the reaction zone, such that the opening may be (i) opened for the delivery of each of the air sample and the optional target analyte, the freely mobile enzyme, and the freely mobile substrate to the reaction zone or chamber, and subsequently (ii) closed when desired.

Another preferred embodiment of the method of this invention provides including wherein the direction of air flow is at a ninety degree angle from the first end of the reaction zone towards the surface of the collection matrix.

The method, as described herein, includes providing the freely mobile enzyme that is selected from the group of an oxidoreductase, a transferase, a hydrolase, a lyase, and an isomerase. In a preferred embodiment, the freely mobile enzyme is a hydrolase enzyme. In another embodiment of the method of this invention, as described herein, includes providing the freely mobile enzyme that is an acetylcholinesterase or a butyrylcholinesterase and the target analyte that is a cholinesterase inhibitor. Another embodiment of the method of this invention provides wherein the freely mobile enzyme is a chloroperoxidase or is an alcohol oxidase. Another embodiment of the method of the present invention, as described herein, includes providing the freely mobile substrate that is selected from the group consisting of an acetylcholine, a butyrylcholine, an indoxylacetate, and a resofurin, and wherein the freely mobile enzyme is selected from the group of an acetylcholinesterase and a butyrylcholinesterase. A further embodiment of the present invention as described herein includes providing the freely mobile substrate that is a benzoyl-arginine-ethyl-ester and the freely mobile enzyme that is a papain. In yet another embodiment of this invention as described herein the method includes providing the freely mobile substrate that is an urea and the freely mobile enzyme that is an urea aminohydrolase. In another embodiment of this invention, the method, as described herein, includes delivering the freely mobile enzyme to the reaction zone wherein the freely mobile enzyme is selected from the group consisting of peroxidase, chloroperoxidase, alkaline phosphatase, and alcohol oxidase, and combinations thereof. A further embodiment of this invention provides a method, as described herein, including delivering the freely mobile substrate to the reaction zone wherein the freely mobile substrate is selected from the group consisting of amplex red, tyrosine, fluorescein diphosphate, peroxidase and amplex red, and combinations thereof. Another embodiment of the method of the present invention, as described herein, includes delivering the freely mobile substrate to the air sample wherein the freely mobile substrate is dissolved in a solvent, such as for example but not limited to, water.

It will be appreciated by those persons skilled in the art that there are many enzyme/substrate combinations that may be employed in the methods and device of the present invention. For example, but not limited to, the following enzyme/substrate combinations may be employed: peroxidase/Amplex red; Chloroperoxidase/Tyrosine; Alkaline phosphatase/Fluorescein diphosphate; and Alcohol oxidase/coupled with peroxidase and amplex red.

The method, as described herein, preferably includes alternating the flow of intermittent delivery of the air sample, the freely mobile enzyme, and the freely mobile substrate, respectively, in any order of addition, to the reaction zone to form a cycle of entrainment of the freely mobile enzyme and freely mobile substrate, with the air sample and optionally the target analyte, in the reaction zone to produce a plurality of the optical reporters. in a more preferred embodiment of the present invention as described herein, the method includes providing the intermittent addition of the freely mobile enzyme initially to the reaction zone, followed by the intermittent addition of the freely mobile enzyme substrate to the reaction zone to form a cycle of entrainment of the freely mobile enzyme and freely mobile substrate, with the air sample and optionally the target analyte, in the reaction zone to produce a plurality of the optical reporters.

Another embodiment of the method of the present invention as described herein includes first delivering the freely mobile enzyme to the reaction zone in the direction of the collection matrix before delivering the air sample, the optional target analyte, and the freely mobile substrate to the reaction zone in the direction of the collection matrix. This embodiment provides for the freely mobile enzyme to contact the collection matrix before the air sample and the optional target analyte and the enzyme substrate contacts the collection matrix.

The method, as described herein, includes providing a complete cycle, as described herein, having a time period greater than about thirty seconds to about ten minutes, and preferably within 5 minutes.

The method, as described herein, includes providing the signal that is a response selected from the group consisting of a fluorescent response, a phosphorescent response, a chemiluminescent response, and a colorimetric response, and combinations thereof.

In yet another embodiment of this invention, the method, as described herein, includes providing a computer for recording and storing data that is read from the detector or detectors. Further, the method, as described herein, includes analyzing the data stored on the computer. Preferably, the method, as described herein, includes providing wherein the data is directly output from the detector. More preferably, the method, as described herein, includes providing wherein the data is wirelessly transmitted by the detector.

Another embodiment of the present method, as described herein, includes delivering the freely mobile enzyme, the freely mobile substrate, and the air sample and the optional analyte in any order of addition, either separately or simultaneously, to the reaction zone.

The method, as described herein, includes providing at least one wave excitation source that is a laser source or a LED source for providing excitation wavelengths in the range from 220 nanometers to 1500 nanometers. The wave excitation source may be a single laser used in concert with harmonic generation techniques. Preferably, the method includes providing wherein the one or more of the wavelength excitation source operates in a modulated manner or as a continuous wave source. For the modulated sources, a modulation rate of 10 MHz or greater is preferred.

Preferably the method, as described herein, includes providing a reaction zone having at least one opening located at the first end of the reaction zone and at least one opening located at the second end of the reaction zone. Preferably, the method, as described herein, includes providing wherein the first end of the reaction zone is located opposite of the second end of the reaction zone.

The method, as described herein, includes delivering the air sample and optionally the target analyte, the freely mobile enzyme, and the freely mobile substrate to the reaction zone using a fan.

Another embodiment of this invention provides an enzyme-based air monitoring device (sensor) for detecting a target analyte in air. FIG. 1 shows a preferred embodiment of the enzyme-based air monitoring device (1) of this invention for detecting a target analyte in air comprising at least one chamber (3) having a first end (5) and a second end (7) and a middle section (9) disposed between the first end (5) and the second end (7), wherein the chamber (3) has at least one opening (11) located at the first end (5) of the chamber (3); a mechanism (13) for providing an air flow within the chamber for continuously or intermittently delivering an air sample optionally containing a target analyte to the first end (5) of the chamber (3) through the opening (11) in the chamber; a mechanism (15) for delivering a freely mobile enzyme to the air flow [i.e the air flow is shown in FIG. 1 by the arrow starting at the air inlet and continuing through the opening (11) of the chamber (3) and continuing from the first end (5) of the chamber (3) through the second end (7) of the chamber (3)] within the chamber (3) containing the air sample and the optional target analyte, wherein the freely mobile enzyme is in a nebulized, aerosolized, or gaseous form; a mechanism (17) for delivering a freely mobile substrate to the air flow within the chamber containing the air sample and the optional target analyte, wherein the freely mobile substrate is in a nebulized, aerosolized, gaseous, or aqueous form; a chemical reaction zone (19) located within an interior (21) of the chamber (3) for the entrainment of the freely mobile enzyme, and the freely mobile substrate, within the air sample containing an optional target analyte for producing a biocatalytic reaction product of a plurality of freely mobile biocatalytic optical reporters (shown in FIG. 1 as the "sensing element"), without adsorbtion of the enzyme onto a surface of the air sample and the optional target analyte; a collection matrix (23) located within the interior (21) of the chamber (3) and positioned below the chemical reaction zone (19), the collection matrix (23) having a surface (25) located within the interior (21) of the chamber (3) or in juxtaposition to the interior wall (26) of the chamber (3); a mechanism [which may be the same mechanism as 13 as shown in FIG. 1, or an additional mechanism (not shown in FIG. 1)] for directing the air flow containing at least one of the freely mobile biocatalytic optical reporters (sensing element of FIG. 1) to the surface of the collection matrix [i.e see the air flow represented by the arrows shown in FIG. 1 in the interior of the chamber of the device]; a set of optics located within the chamber (3) comprising at least one wave excitation source (not shown in FIG. 1) for generating and emitting at least one discrete wavelength of light, a mechanism for directing at least one discrete wavelength of light (not shown in FIG. 1) to the surface of the collection matrix (25) having at least one of the biocatalytic optical reporters (sensing element), and at least one detector (not shown in FIG. 1) for (a) reading (i) a signal of reflected, absorbed light or a light response from at least one of the plurality of the optical reporters (sensing element) located on the surface (25) of the collection matrix (23), or (ii) an absence or suppression of a signal of reflected, absorbed light or absence or suppression of a light response from at least one of the plurality of the optical reporters (sensing element) located on the surface (25) of the collection matrix (23), and (b) detecting (i) an increase or a decrease of the presence of the signal, or (ii) an absence of the signal; and a mechanism (22) for evacuating the air sample, the optional target analyte, the freely mobile enzyme, the freely mobile substrate, and the biocatalytic optical reporters (sensing element) from the chamber (3) and the collection matrix (23) through the opening (11), or as shown in FIG. 1 through an optional second opening (27) located at the second end (7) of the chamber (3). As shown in FIG. 1, the set of optics (which comprises at least one wave excitation source, a mechanism for directing at least one discrete wavelength of light to the surface of the collection matrix, and at least one detector for reading the signal) interfaces with a computer (29) of the device (1). Further, in another embodiment, the computer (29) reads and stores data output from the optic's detector and the computer analyzes the data to determine if the air sample is contaminated. The device further includes a mechanism (22) for evacuating the interior (19) of the chamber (3) and the surface (25) of the collection matrix (23). Mechanism (22) provides at least one of a product rinse in an aerosol, nebulized or gaseous form to the surface (25) of the collection matrix (23) for removing the air sample, the enzyme, the substrate, the optional target analyte if any, and the biocatalytic optical reporters (sensing element) from the reaction zone (19) and the collection matrix (23). A spent product rinse is formed comprising the air sample, the enzyme, the substrate, the optional target analyte if any, and the biocatalytic optical reporters, which is evacuated from the chamber (3) in FIG. 1, by mechanism (13) through the opening (27) of the chamber. Mechanism (22) effects the regeneration of the collection matrix for reuse and completes one cycle of detection The device, as described herein, includes wherein the mechanism for providing the air flow within the chamber, the mechanism for delivering the freely mobile enzyme to the air sample, the mechanism for delivering the freely mobile substrate, and the mechanism for directing the air flow to the surface of the collection matrix is selected from the group of a fan, an air pump, and combinations thereof.

The device, as described herein, preferably includes wherein the wave excitation source is a laser source or a LED source for providing excitation wavelengths in the range from 220 nanometers to 1500 nanometers. More preferably, the device, as described herein includes wherein the wave excitation source operates in a modulated manner or in a continuous manner.

In yet another embodiment of the device of this invention, as described herein, the chamber has at least one opening located at the first end of the chamber and at least one opening located at the second end of the chamber. More preferably, the device, as described herein, includes wherein the first end of the chamber is located opposite of the second end of the chamber.

Another embodiment of the device, as described herein, includes wherein the mechanism for evacuating the chamber is selected from the group consisting of a fan, an air pump, a vacuum, and combinations thereof.

A further embodiment of this device, as described herein, includes an alarm that is activated if a target analyte is detected by the detector.

Another embodiment of the present invention provides a device, as described herein, further comprising the reaction zone and chamber that is temperature controlled having a temperature ranging from zero degrees Centigrade to ninety five degrees Centigrade. A further embodiment of this invention includes providing a separate storage zone for housing the freely mobile enzyme and a separate storage zone for housing the freely mobile substrate. Each storage zone is operatively connected to an air sample flow conduit. One end of the air sample flow conduit is operatively connected to the exterior wall of the chamber at the location of the opening. When the opening of the chamber (i.e. the opening leading to the reaction zone of the chamber) is in the unsealed state, the air flow proceeding through the air sample flow conduit (intake of the air sample and optional target analyte from the environment or from a collected sample occurs at the second end of the air sample flow conduit) in the direction of the opening of the reaction zone enters the opening and flows into the reaction zone of the chamber. In a preferred embodiment of this invention, each separate storage zone is temperature controlled such that the storage zone for each of the enzyme and each of the enzyme substrate have a temperature ranging from zero degrees Centigrade to ninety five degrees Centigrade, respectively.

It will be appreciated by those persons skilled in the art that the present invention provides a device (sensor) and methods for detecting, classifying and identifying particles, aerosols and/or vapor in the air. The sensor includes an air flow conduit operatively connected to a chamber having a reaction zone for providing/directing an environmental sample (either an air sample taken directly from the present environment or an air sample taken from a previously collected sample from a remote location) of particles, aerosols and/or vapors to a collection matrix having a porous surface. This collection matrix is also referred to herein as an impactor disk. the collection matrix or impactor disk may be varied in terms of material, pore size, thickness and surface properties. The device also includes at least one mechanism for directing an aerosol of biocatalytic optical receptors to the porous surface of the collection matrix. Another element of the device is at least one wave excitation source for generating and emitting discrete wavelengths of light and a mechanism for directing the wavelengths of light (i.e light energy) to the surface of the collection matrix. At least one detector reads the reflected, adsorbed light response and/or fluorescence response, and/or a phosphorescent response, and/or a chemiluminescent response, and/or a colorimetric response. The same detectors can be used to read the suppression of reflected, adsorbed light and/or fluorescence response. As a final step the device optionally operates repetitive cycles and regenerates the surface of the porous collection matrix in each repetitive cycle.

Preferably, the device draws air into the air sample flow conduit from the environment at a flow rate of 1 liter per minute. Sampling flow rate can be varied from 0.1 liter to 10 liters per minute. The device operates continuously in repetitive cycles; first enzyme aerosol is added to the air stream in the air sample flow conduit, after a sampling time which can range from 1 second to 10 minutes, substrate aerosol (enzyme reagent) is added to the air sample flow conduit. All air sample with or without a target analyte, the enzyme and the substrate flows in the air sample flow conduit to the reaction zone of the chamber. At that point the air pump, effecting the flow of the air sample, substrate and enzyme through the air sample flow conduit, is shut off, and the opening to the reaction zone of the chamber of the device is preferably resealed to observe the progress of the biocatalytic enzyme reaction in the reaction zone at the surface of the porous collection matrix. The observation time could range from 10 seconds to greater than 90 seconds.

It will be appreciated from the Figures that the final step of the cycle comprises rinsing the enzyme(s), substrate(s), and enzyme reaction product (optical reporters) off of the surface of the collection matrix. After the rinse step a new cycle is immediately started by adding enzyme aerosol to the reaction zone for contacting the surface of the surface of the porous collection matrix (impactor disk). The cycle time can be varied between 1 minute and 15 minutes. Each cycle generates a signal based on a colorimetric, autofluorescence, phosphorescent, and/or luminescent reaction. The absence of this signal/reaction indicates the presence of the target analyte (i.e. a contaminant chemical).

Due to the fact that this method and device utilizes a highly specific enzyme reaction as a sensing method it displays a much higher resistance to interferences compared to standard electronic sensing methods. The method of the present invention detects protein molecules specifically enzyme and/or enzymatic substrates.

One embodiment of this invention is to provide a method to detect vapors of cholinesterase inhibitors at extremely low concentrations without interference by other chemicals being present in the environment. In this embodiment the device illustrated in FIG. 1 uses one air pump to draw air from the environment and direct the air to the surface of the collection matrix (impactor disk) within the reaction zone. In this embodiment the air is drawn at a flow rate of 1 liter per minute. The sampling flow rate can be varied between 0.1 and 10 liter per minute. The device also includes at least three nebulizers which periodically provide aerosols to the reaction zone and the biocatalytic chemical reaction taking place at the surface of the collection matrix. In addition the device also includes a mechanism (optics) to direct light onto the surface of the collection matrix and a detector to read an optical signal originating from the biocatalytic reaction product of a plurality of optical reporters (i.e. the sensing reaction).

In this embodiment of the invention, the device and method operates in repetitive cycles ranging from 30 seconds to 10 minutes. Cycles typically, for example, comprise 6 steps as shown in FIG. 2: 1) enzyme addition, 2) sampling, 3) substrate addition, 4.1) reading time, 4.2) alarm status update, and 5) rinse. The cycle shown in FIG. 2 took 5 minutes for completion. The enzyme and substrate addition took 5 seconds, the sampling time took 115 seconds, the reading took 85 seconds and was concluded by the alarm status update at the end which requires only a fraction of a second, and the rinse took 90 seconds. Each cycle concludes with the rinse step where components of the reaction are rinsed off the surface of the collection matrix and preferably from the reaction zone and the surface of the collection matrix, in order to set the stage for a new sampling cycle.

FIGS. 3*a* and 3*b* illustrate the steps of one 5 minute cycle with no detection event in more detail. As shown in FIG. 3*a*, during the first step 1) 5 seconds enzyme addition, the air pump is actively pumping air from the environment through the system. Particles, aerosols and vapor from the environment are collected on the impactor disk or surface of the collection matrix. During this step one nebulizer is activated adding aerosolized enzyme visualized in FIGS. 3*a* and 3*b* by clam shaped symbols. The enzyme is being accumulated on the impactor disk/surface of the collection matrix. During the next step 2) 115 seconds sampling, the air pump continues to pump air visualized in FIG. 3*a* with dotted lines from the environment through the device. With no detectable targets in the environment during sampling no change occurs to the enzyme molecule. In FIG. 3*b*, the sampling period is followed by step 3) 5 seconds substrate addition, where the system adds aerosolized substrate utilizing another nebulizer to the air stream drawn by the air pump. The substrate molecules visualized in FIG. 3*b* by pie looking symbols bind to the enzyme molecules. The binding process is visualized in FIG. 3*b* where both the enzyme and substrate symbols bind together similar to a puzzle. During the next step 4) 85 seconds reading, the catalytic reaction of the enzyme substrate complex is monitored with an optical system. In this embodiment the enzyme, acetylcholinesterase, cleaves the substrate indoxyl acetate to acetic acid and a fluorescent compound. This fluorescent compound is detectable with an excitation of 405 nm and an emission of 470 nm. During the reading period, the air sampling pump is typically switched off. At the conclusion of the reading period the signal interpretation occurs with the alarm status update indicating a detectable event or in the case of FIGS. 3*a* and 3*b* a non detectable event. The cycle is concluded with the final step 5) rinse, where a third nebulizer is adding a rinse liquid to the air stream from the environment. The rinse or washing liquid removes the enzyme, reaction products and any un-reacted substrate molecules off the impactor disk/surface of the collection matrix. This allows the resetting of the sampling area for a subsequent cycle.

FIG. 4 illustrates the identical 5 minute cycle shown in FIGS. 3*a* and 3*b* except that there are detectable targets/ enzyme inhibitors in the environment. In FIG. 4, those enzyme inhibitors visualized by odd shaped pie symbols (see step 2 of FIG. 4) are drawn from the environment during steps 1) enzyme addition and 2) sampling. The enzyme inhibitor molecules bind to the enzyme molecule, rendering the enzyme non functional by blocking the active binding site— enzyme inhibition occurs. Substrate molecules added during step 3) substrate addition are not able to bind to the active site of the enzyme molecules preventing the biocatalytic reaction from taking place, preventing the generation of the fluorescent product and the absence of an optical signal during step 4) reading period. The absence of an optical signal during step 4 triggers the alarm status at the conclusion of step 4 resulting in an alarming of the system.

One of the key aspects of this invention is the fact that the catalytic enzyme reaction is extremely fast and could be in the thousands of reactions occurring per second depending on the enzyme/substrate combination and concentration utilized. This fact allows for a very powerful amplification effect as only a few target molecules from the environment are sufficient to shut down reactions ranging in the thousands per second. This means that the method and device described in this invention is very sensitive and very specific as the enzyme substrate binding is very specific and other chemicals in the environment do not affect the sensing reaction unlike in other electronic sensing mechanism where the detector senses any chemical and has to rely on separation techniques or other highly sophisticated identification methods.

EXAMPLES

Example 1

Example 1 provides a means to detect dichlorvos (ddvp) vapor. The device of the invention in this example was operated continuously in 4 minute cycles. Each cycle consists of a second enzyme addition step, a two minute sampling period at a flow rate of 1 liter per minute, a 6 second substrate addition step, a 1 minute reading period and a 49 second rinse step. The consumables/reagents consisted of a) 3 mg/ml acetylcholinesterase enzyme solution in buffer, b) 12.5 mg/ml indoxyl acetate substrate solution in isopropyl alcohol (IPA) and c) 100 mM buffer at pH 7.0. Those persons skilled in the art appreciate that the substrate can be dissolved in many other suitable solvents. This example used a polypropylene disk with a pore size of 120 um and a thickness of 1.6 mm as the impactor disk (collection matrix). The impactor disk can be varied in material, pore size and thickness. The enzyme aerosol was generated with 5×500 ms pulses every second for 5 seconds total. The substrate aerosol was generated using 5×50 ms pulses every second for 5 seconds total. The substrate addition was followed by a 1000 ms buffer rinse to enable solubilizing the substrate in buffer. The rinse step at conclusion of the cycle was accomplished by continuously aerosolizing buffer for about 49 seconds.

The various steps of the cycle are visualized with symbols on the time axis of the data shown in FIG. 5. FIG. 5 shows two cycles. The first cycle between the times of 13:40:30 and 13:44:30 shows no detection event and the second cycle between 13:44:30 and 13:47:30 shows a detection event. The enzyme additions at the beginning of each cycle are visualized with solid circles, the substrate additions are visualized with solid squares and the beginning of the rinse steps are visualized with white squares. Sampling occurs between enzyme addition (solid circles) and substrate addition (solid squares). The reading time takes place between the substrate addition (solid squares) and the beginning of the rinse step (white squares).

Example 1 demonstrates a typical detection event. The first cycle resulted in a signal amplitude of around 8,000 fluorescent units indicating no enzyme inhibition and the absence of the target chemicals. The second cycle shows a detection event. The second cycle after sampling of dichlorvos vapor visualized by a solid triangle resulted in a signal amplitude of around 500 indicating the absence of enzyme activity due to inhibition of the acetylcholinesterase enzyme by dichlorvos. The loss of amplitude resulted in an alarm at the end of the reading step indicated by the diamond. Dichlorvos vapor was sampled from an airtight 27 liter acrylic chamber. 110 ul of dichlorvos solution in isopropanol (IPA) at a concentration of 5 ul dichlorvos per 5.5 ml IPA was added through a septum onto a petri dish inside that chamber. A small fan facilitated the rapid evaporation of the dichlorvos/IPA solution.

Example 2

Example 2 provides another method of the present invention to detect dichlorvos (DDVP) vapor. This example shows that the impactor disk (collection matrix) can be varied in material, pore size and thickness. This example used a polyethylene disk with a pore size of 15-45 um and a thickness of 1.6 mm as the impactor disk. The device of the present invention in this example was operated continuously in 4 minute cycles. Each cycle consists of a 5 second enzyme addition step, a two minute sampling period at a flow rate of 1 liter per minute, a 6 second substrate addition step, a 1 minute reading period and a 49 second rinse step. The consumables/reagents consisted of a) 3 mg/ml acetylcholinesterase enzyme solution in buffer, b) 12.5 mg/ml indoxyl acetate substrate solution in isopropyl alcohol (IPA) and c) 100 mM buffer at pH 7.0. The enzyme aerosol was generated with 5×500 ms pulses every second for 5 seconds total. The substrate aerosol was generated using 5×50 ms pulses every second for 5 seconds total. The substrate addition was followed by a 1000 ms buffer rinse to enable solubilizing the substrate in buffer. The rinse step at conclusion of the cycle was accomplished by continuously aerosolizing buffer for about 49 seconds.

Example 2 demonstrates another detection event. As shown in FIG. 6, the first two cycles resulted in a signal amplitude of around 22,000 fluorescent units indicating no enzyme inhibition and the absence of the target chemicals. The third and fourth cycles shows a detection event. The second cycle after sampling of dichlorvos vapor visualized by a solid triangle resulted in a signal amplitude of less than 9,000 fluorescent units indicating the absence of enzyme activity due to inhibition of the acetylcholinesterase enzyme by dichlorvos. The loss of amplitude resulted in an alarm at the end of the reading step indicated by the diamond. Dichlorvos vapor was sampled from an airtight 27 liter acrylic chamber. 110 ul of dichlorvos solution in isopropanol (IPA) at a concentration of 5 ul dichlorvos per 5.5 ml IPA was added through a septum onto a petri dish inside that chamber. A small fan facilitated the rapid evaporation of the dichlorvos/IPA solution. The fifth amplitude after removal of dichlorvos contamination shows a recovery of signal resulting in an increase of the signal amplitude.

Example 3

Example 3 provides another method of the present invention to detect dichlorvos (DDVP) vapor. This example shows that the cycle times can be varied, and that the substrate can be delivered in aqueous form. The device of the present invention in this example was operated continuously in 2.5 minute cycles. Each cycle consists of a 5 second enzyme addition step, a 55 second sampling period at a flow rate of 1 liter per minute, a 5 second substrate addition step, a 55 second reading period and a 30 second rinse step. The consumables/reagents consisted of a) 3 mg/ml acetylcholinesterase enzyme solution in buffer, b) 12.5 mg/ml indoxyl acetate substrate solution in isopropyl alcohol (IPA), diluted in buffer 100 fold and c) 100 mM buffer at pH 7.0. This example used a polypropylene disk with a pore size of 120 um and a thickness of 1.6 mm as the impactor disk (collection matrix). The enzyme aerosol was generated with 5×500 ms pulses every second for 5 seconds total. The substrate aerosol was generated using 5×500 ms pulses every second for 5 seconds total. The rinse step at conclusion of the cycle was accomplished by continuously aerosolizing buffer for about 30 seconds.

Example 3 shows multiple detection events. As set forth in FIG. 7, the first three cycles resulted in a signal amplitude of around 7,000 fluorescent units indicating no enzyme inhibition and the absence of the target chemicals. The fourth and fifth cycles shows a detection event. The fourth cycle overall which is the first cycle after sampling of dichlorvos vapor visualized by a solid triangle resulted in a signal amplitude of less than 500 fluorescent units indicating the absence of enzyme activity due to inhibition of the acetylcholinesterase enzyme by dichlorvos. The loss of amplitude resulted in an alarm at the end of the reading step indicated by the diamond. Dichlorvos vapor was sampled from an airtight 27 liter acrylic chamber. 110 ul of dichlorvos solution in isopropanol (IPA) at a concentration of 5 ul dichlorvos per 5.5 ml IPA was added through a septum onto a petri dish inside that chamber. A small fan facilitated the rapid evaporation of the dichlorvos/IPA solution. The sixth, seven and eighth cycles overall, after removal of dichlorvos contamination show a recovery of signal resulting in an increase of the signal amplitude. The ninth and tenth cycle show a second detection event with loss of amplitude. The subsequent five cycles show another signal recovery and detection event.

Example 4

Example 4 provides the method of the present inventions to detect aerosolized paraoxon. This example shows that the device of this invention is capable to detect other physical forms besides vapor. The device of this invention in this example was operated continuously in 4 minute cycles. Each cycle consists of a 5 second enzyme addition step, a two minute sampling period at a flow rate of 1 liter per minute, a 6 second substrate addition step, a 1 minute reading period and a 49 second rinse step. The consumables/reagents consisted of a) 3 mg/ml acetylcholinesterase enzyme solution in buffer, b) 12.5 mg/ml indoxyl acetate substrate solution in isopropyl alcohol (IPA) and c) 100 mM buffer at pH 7.0. This example used a polyethylene disk with a pore size of 15-45 um and a thickness of 1.6 mm as the impactor disk. The enzyme aerosol was generated with 5×500 ms pulses every second for 5 seconds total. The substrate aerosol was generated using 5×50 ms pulses every second for 5 seconds total. The substrate addition was followed by a 1000 ms buffer rinse to enable solubilizing the substrate in buffer. The rinse step at conclusion of the cycle was accomplished by continuously aerosolizing buffer for about 49 seconds.

Figure 8:
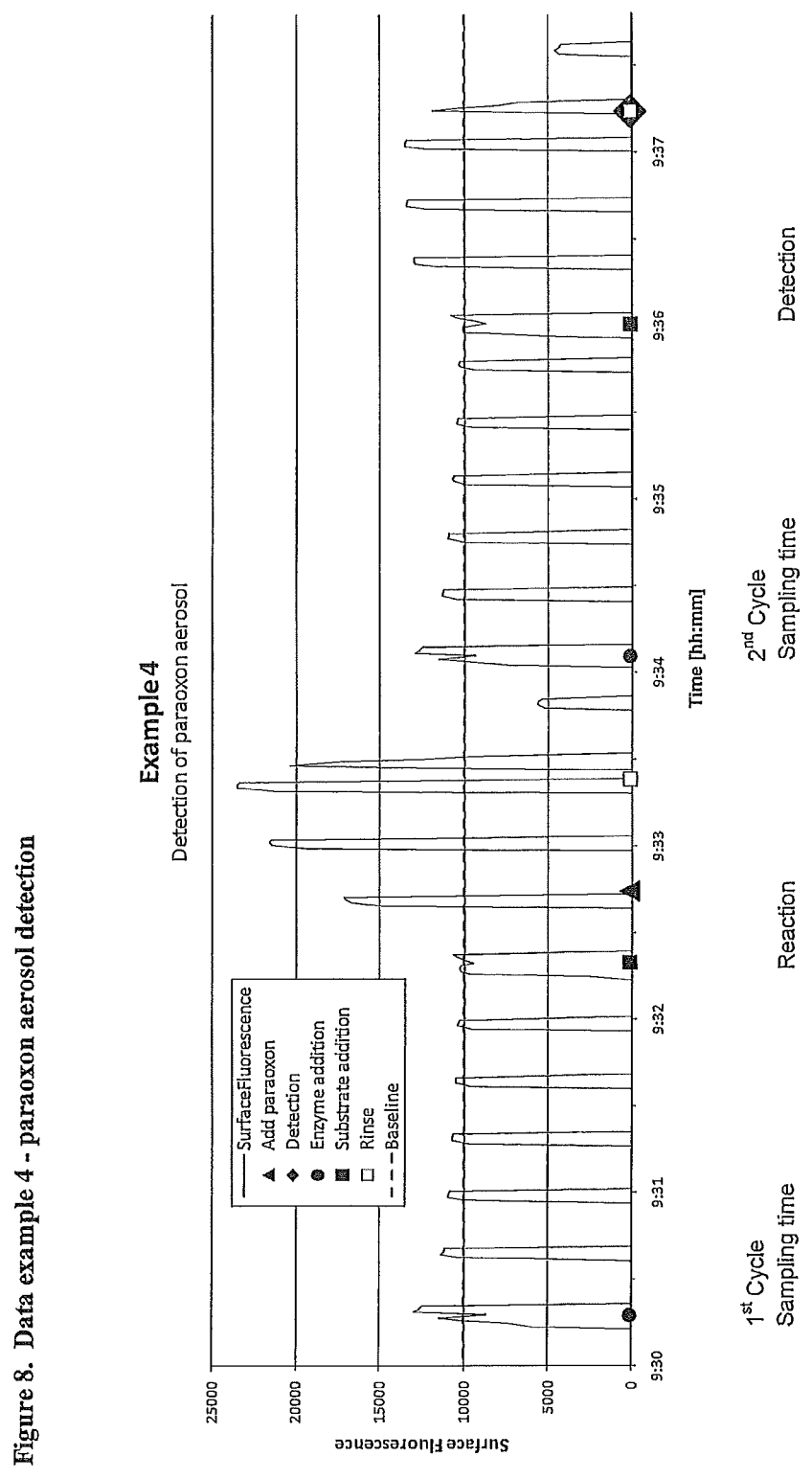

Example 4 shows another detection event. FIG. 8 shows that in Example 4, aerosolized paraoxon was detected. In Example 4, other physical forms besides vapor were detected. The first cycle resulted in a signal amplitude of around 14,000 fluorescent units indicating no enzyme inhibition and the absence of the target chemicals. The second cycle shows a detection event. The second cycle after sampling of aerosolized paraoxon visualized by a solid triangle resulted in a signal amplitude of around 4,000 indicating the absence of enzyme activity due to inhibition of the acetylcholinesterase enzyme by dichlorvos. The loss of amplitude resulted in an alarm at the end of the reading step indicated by the diamond. Aerosolized paraoxon was generated using a 2.5 ppm paraoxon solution aerosolized with a nebulizer attached to an airtight plastic chamber. The nebulizer was operated every 10 seconds for a pulse of 10 milliseconds.

Example 5

Example 5 provides another method of this invention to detect dichlorvos (DDVP) vapor. This is another example showing that the cycle times can be varied. The system in this example was operated continuously in 1 minute cycles. Each cycle consists of a 5 second enzyme addition step, a 10 second sampling period at a flow rate of 1 liter per minute, a 5 second substrate addition step, a 25 second reading period and a 15 second rinse step. The consumables/reagents consisted of a) 3 mg/ml acetylcholinesterase enzyme solution in buffer, b) 12.5 mg/ml indoxyl acetate substrate solution in isopropyl alcohol (IPA), diluted in buffer 100 fold and c) 100 mM buffer at pH 7.0. This example used a polyethylene disk with a pore size of 15-45 um and a thickness of 1.6 mm as the impactor disk. The enzyme aerosol was generated with 5×500 ms pulses every second for 5 seconds total. The substrate aerosol was generated using 5×500 ms pulses every second for 5 seconds total. The rinse step at conclusion of the cycle was accomplished by continuously aerosolizing buffer for about 15 seconds.

Example 5 shows another detection event. As shown in FIG. 9, the first three cycles resulted in a signal amplitude of around 3,000 fluorescent units indicating no enzyme inhibition and the absence of the target chemicals. The fourth, fifth and sixth cycles shows a detection event. The fourth cycle overall which is the first cycle after sampling of dichlorvos vapor visualized by a solid triangle resulted in a signal amplitude of less than 1,000 fluorescent units indicating the absence of enzyme activity due to inhibition of the acetylcholinesterase enzyme by dichlorvos. The loss of amplitude resulted in an alarm at the end of the reading step indicated by the diamond. Dichlorvos vapor was sampled from an airtight 27 liter acrylic chamber. 110 ul of dichlorvos solution in isopropanol (IPA) at a concentration of 5 ul dichlorvos per 5.5 ml IPA was added through a septum onto a petri dish inside that chamber. A small fan facilitated the rapid evaporation of the dichlorvos/IPA solution. The subsequent six cycles show another example how the system is able to recovery.

Example 6

Example 6 provides a method of this invention for the detection of a protein in the air. The device in this example was operated continuously in 3 minute cycles. Each cycle consists of a 30 second sampling period at a flow rate of 1 liter per minute, a 5 second substrate addition step, a 85 second reading period and a 60 second rinse step. The consumables/reagents consisted of a) 12.5 mg/ml indoxyl acetate substrate solution in isopropyl alcohol (IPA), diluted in buffer 100 fold and b) 100 mM buffer at pH 7.0. This example used a polyethylene disk with a pore size of 15-45 um and a thickness of 1.6 mm as the impactor disk. The substrate aerosol was generated using 5×500 ms pulses every second for 5 seconds total. The rinse step at conclusion of the cycle was accomplished by continuously aerosolizing buffer for about 60 seconds.

Example 6 shows the detection of a protein. Specifically, acetylcholinesterase enzyme solution was aerosolized into a plastic test chamber at a concentration of 3 mg/ml. The sampled air was contaminated with enzyme two times at intervals indicated by solid triangles (beginning) and white triangles (end). As set forth in FIG. 10, the device indicated the presence of the target protein by an amplitude increase to at least 2,000 fluorescent units in cycles four, five and six compared to an amplitude of 0 in cycles one, two and three during the time clean air was sampled. Example 6 also shows that the device is able to fully recover and demonstrate a second detection event.

Example 7

Example 7 provides a method of this invention to detect other chemicals in the air. The device in this example was operated continuously in 4 minute cycles. Each cycle consists of a 2 minute second sampling period at a flow rate of 1 liter per minute, 5 second enzyme addition step, a 85 second reading period and a 30 second rinse step. The consumables/reagents consisted of a) 3 mg/ml acetylcholinesterase enzyme solution in buffer and b) 100 mM buffer at pH 7.0. This example used a polyethylene disk with a pore size of 15-45 um and a thickness of 1.6 mm as the impactor disk. The enzyme aerosol was generated using 5×500 ms pulses every second for 5 seconds total. The rinse step at conclusion of the cycle was accomplished by continuously aerosolizing buffer for about 30 seconds.

Example 7 shows the detection of a specific chemical. Specifically, indoxyl acetate solution was aerosolized into a plastic test chamber at a concentration of 0.1 mg/ml. FIG. 11, shows that the sampled air was contaminated with indoxyl acetate two times at intervals indicated by solid triangles (beginning) and white triangles (end). The device indicated the presence of the target protein by an amplitude increase to at least 3,000 fluorescent units in cycles three and four compared to an amplitude of 500 in cycles one and two during the time clean air was sampled. Example 7 also shows that the device is able to fully recover and demonstrate a second detection event.

Whereas particular embodiments of the instant invention have been described for the purposes of illustration, it will be evident to those persons skilled in the art that numerous variations and details of the instant invention may be made without departing from the instant invention as defined in the appended claims.

What is claimed is:

1. A method for detecting, classifying, and identifying a target analyte in air comprising the steps of:

providing an air flow mechanism for continuously or intermittently delivering an air sample optionally containing a target analyte to a reaction zone wherein the reaction zone has a first end and a second end and a middle section disposed between said first end and said second end, wherein said reaction zone has at least one opening for receiving said air sample;

providing a collection matrix having a surface within or in juxtaposition to said reaction zone;

establishing a direction of air flow of said air sample from said opening of said reaction zone towards said surface of said collection matrix;

introducing through said opening of said reaction zone either continuously or intermittently at least one freely mobile enzyme, and at least one freely mobile substrate to said air sample, wherein said freely mobile enzyme, and said freely mobile substrate are in a nebulized, aerosolized, gaseous, or aqueous form;

providing for the entrainment of said freely mobile enzyme, and said freely mobile substrate with said air sample in said reaction zone for producing a biocatalytic chemical reaction of said air sample, said enzyme, said substrate, and optionally said target analyte, for forming a biocatalytic reaction product of a plurality of freely mobile biocatalytic optical reporters, without effecting adsorbtion of said enzyme onto a surface of said air sample or said optional target analyte;

directing the air flow within said reaction zone with said plurality of said biocatalytic optical reporters in the direction of said surface of said collection matrix for contacting said surface of said collection matrix with at least one of said plurality of said biocatalytic optical reporters;

providing at least one wave excitation source for providing at least one discrete wavelength of light;

directing at least one of said discrete wavelength of light to said surface of said collection matrix having at least one of said plurality of said biocatalytic optical reporters;

providing one or more detectors for reading (i) a signal of reflected, absorbed light or a light response from said one or more optical reporters located on said surface of said collection matrix, or (ii) an absence or suppression of a signal of reflected, absorbed light or absence or suppression of a light response from said one or more optical reporters located on said surface of said collection matrix;

detecting (i) an increase or a decrease of the presence of said signal, or (ii) an absence of said signal; and providing at least one of a product rinse in an aerosol, nebulized or gaseous form to said surface of said collection matrix for removing said air sample, said enzyme, said substrate, said optional target analyte if any, and said biocatalytic optical reporters from said reaction zone and said collection matrix, and forming a spent product rinse comprising said air sample, said enzyme, said substrate, said optional target analyte if any, and said biocatalytic optical reporters for effecting regeneration of said collection matrix for reuse;

evacuating said spent product rinse from said reaction zone and said collection matrix via at least one of said openings in said reaction zone for completing one cycle of detection;

and optionally repeating one or more cycles of the above steps.

2. The method of claim 1 including delivering said air sample to said reaction zone either passively or actively.

3. The method of claim 1 including delivering said air sample to said reaction zone wherein said air sample is a collected air sample.

4. The method of claim 1 including providing a temperature controlled reaction zone having a temperature ranging from zero degrees Centigrade to ninety five degrees Centigrade.

5. The method of claim 1 including providing a temperature controlled enzyme and/or substrate having a temperature ranging from zero degrees Centigrade to ninety five degrees Centigrade.

6. The method of claim 1 including wherein said surface of said collection matrix is a porous material.

7. The method of claim 6 including wherein said porous material is selected from the group consisting of a polymer, vegetable fibers, lignin, and cellulose, and combinations thereof.

8. The method of claim 7 including wherein said polymer is selected from the group consisting of a polypropylene and a polyethylene, and combinations thereof.

9. The method of claim 1 including providing wherein said one or more openings of said reaction zone are resealable openings for effecting a sealed engagement with said reaction zone and an unsealed relationship with said reaction zone, such that said opening may be (i) opened for said delivery of each of said air sample and said optional target analyte, said freely mobile enzyme, and said freely mobile substrate, and subsequently (ii) closed.

10. The method of claim 1 including providing said direction of air flow at a ninety degree angle from said first end of said reaction zone towards said surface of said collection matrix.

11. The method of claim 1 including providing said freely mobile enzyme that is selected from the group of an oxidoreductase, a transferase, a hydrolase, a lyase, and an isomerase.

12. The method of claim 11 including providing said freely mobile enzyme that is said hydrolase enzyme.

13. The method of claim 1 including providing said freely mobile enzyme that is an acetylcholinesterase or a butyrylcholinesterase and said target analyte that is a cholinesterase inhibitor.

14. The method of claim 1 including providing said freely mobile substrate that is selected from the group consisting of an acetylcholine, a butyrylcholine, an indoxylacetate, and a resofurin, and wherein said freely mobile enzyme is selected from the group of an acetylcholinesterase and a butyrylcholinesterase.

15. The method of claim 1 including providing said freely mobile substrate is a benzoyl-arginine-ethyl-ester and said freely mobile enzyme is a papain.

16. The method of claim 1 including providing said freely mobile substrate that is an urea and said freely mobile enzyme that is an urea aminohydrolase.

17. The method of claim 1 including alternating the flow of intermittent delivery of said air sample, said freely mobile enzyme, and said freely mobile substrate, respectively, in any order of addition, to said reaction zone to form said cycle of entrainment of said freely mobile enzyme and freely mobile substrate, with said air sample and optionally said target analyte, in said reaction zone to produce said plurality of said optical reporters.

18. The method of claim 17 including providing the intermittent addition of said freely mobile enzyme to said reaction zone, followed by the intermittent addition of said freely mobile enzyme substrate to said reaction zone to form said cycle of entrainment of said freely mobile enzyme and freely mobile substrate, with said air sample and optionally said target analyte, in said reaction zone to produce said plurality of said optical reporters.

19. The method of claim 1 including first delivering said freely mobile enzyme to said reaction zone in the direction of said collection matrix before delivering said air sample, said optional target analyte, and said freely mobile substrate to said reaction zone in the direction of said collection matrix.

20. The method of claim 1 including providing said cycle having a time period greater than about thirty seconds.

21. The method of claim 1 including providing said signal that is a response selected from the group consisting of a fluorescent response, a phosphorescent response, a chemiluminescent response, and a colorimetric response, and combinations thereof.

22. The method of claim 1 including providing a computer for recording and storing data that is read from said detector.

23. The method of claim 22 including analyzing said data stored on said computer.

24. The method of claim 22 including wherein said data is directly output from said detector.

25. The method of claim 22 including wherein said data is wirelessly transmitted by said detector.

26. The method of claim 1 including delivering said freely mobile enzyme, said freely mobile substrate, and said air sample and said optional analyte in any order of addition, or simultaneously, to said reaction zone.

27. The method of claim 1 including providing said wave excitation source that is a laser source or a LED source for providing excitation wavelengths in the range from 220 nanometers to 1500 nanometers.

28. The method of claim 27 including providing wherein said wavelength excitation source operates in a modulated manner or in a continuous manner.

29. The method of claim 1 including providing a reaction zone having at least one opening located at said first end of said reaction zone and at least one opening located at said second end of said reaction zone.

30. The method of claim 29 including providing wherein said first end of said reaction zone is located opposite of said second end of said reaction zone.

31. The method of claim 1 including delivering said air sample, said freely mobile enzyme, and said freely mobile substrate, and optionally said target analyte, to said reaction zone using a fan.

32. The method of claim 1 including delivering said freely mobile enzyme to said reaction zone wherein said freely mobile enzyme is selected from the group consisting of peroxidase, chloroperoxidase, alkaline phosphatase, and alcohol oxidase, and combinations thereof.

33. The method of claim 1 including delivering said freely mobile substrate to said reaction zone wherein said freely mobile substrate is selected from the group consisting of amplex red, tyrosine, fluorescein diphosphate, peroxidase and amplex red, and combinations thereof.

34. The method of claim 1 including delivering said freely mobile substrate to said air sample wherein said freely mobile substrate is dissolved in a solvent.

* * * * *